United States Patent [19]

Suzuki et al.

[11] Patent Number: 5,527,908
[45] Date of Patent: Jun. 18, 1996

[54] PYRAZOLOTHIAZOLOPYRIMIDINE DERIVATIVES

[75] Inventors: Fumio Suzuki, Mishima; Yoshisuke Nakasato, Shizuoka; Kenji Ohmori, Mishima; Tadafumi Tamura, Numazu; Soichiro Sato, Shizuoka; Hiroshi Tanaka, Tokyo, all of Japan

[73] Assignee: Kyowa Hakko Kogyo Co., Ltd., Tokyo, Japan

[21] Appl. No.: 94,106

[22] PCT Filed: Dec. 7, 1992

[86] PCT No.: PCT/JP92/01595

§ 371 Date: Aug. 5, 1993

§ 102(e) Date: Aug. 5, 1993

[87] PCT Pub. No.: WO93/12120

PCT Pub. Date: Jun. 24, 1993

[30] Foreign Application Priority Data

Dec. 10, 1991 [JP] Japan ................................. 3-326177

[51] Int. Cl.$^6$ ...................... C07D 513/14; A61K 31/505
[52] U.S. Cl. ............................ 540/548; 544/34; 544/250; 544/251
[58] Field of Search ............................ 544/34, 250, 251; 540/548

[56] References Cited

PUBLICATIONS

Masters et al, J. Amer. Chem Soc., 64, pp. 2709–2712 (1942).
Schmidt et al, Helv. Chim. Acta., 42, pp. 349–359 (1959).
Helvetica Chimica Acta, vol. 54, No. 6 (Sep. 1971) 1687–1691, Bormann et al.
Chemical Abstracts, vol. 84 No. 9 (1976), 59368p., Dashkerich et al.
Jan Svetlik, Liebigs Ann. Chem., vol. 12 (1987) 1121–1122.

*Primary Examiner*—Philip I. Datlow
*Attorney, Agent, or Firm*—Fitzpatrick Cella Harper & Scinto

[57] ABSTRACT

Pyrazolothiazolopyrimidine derivatives represented by the Formula

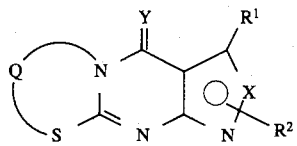

and pharmaceutically acceptable salts thereof are useful as anti-inflammatory, analgesic, immunomodulatory and anti-ulcer agents.

1 Claim, No Drawings

PYRAZOLOTHIAZOLOPYRIMIDINE DERIVATIVES

TECHNICAL FIELD

The present invention relates to pyrazolothiazolopyrimidine derivatives which are useful as anti-inflammatory, analgesic, immunomodulatory and anti-ulcer agents.

BACKGROUND ART 6,7-Dihydro-2-methylpyrazolo[3,4-d]thiazolo[3,2-a]pyrimidin-4(2H)-one which is a tricyclic compound having a 6,7-dihydropyrazolo[3,4-d]thiazolo[3,2-a]pyrimidin-4-one skeleton and which has a substituent on a nitrogen atom at the 2-position is described in Liebigs Ann. Chem., 1121 (1987).

DISCLOSURE OF THE INVENTION

According to the present invention, there can be provided pyzazolothiazolopyrimidine derivatives represented by the following Formula (I):

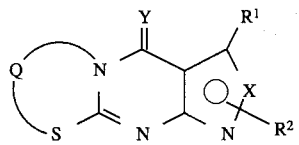

in which $R^1$ represents hydrogen, substituted or unsubstituted lower alkyl, substituted or unsubstituted aryl, substituted or unsubstituted aralkyl, halogen or —$NR^3R^4$ (in which $R^3$ and $R^4$ represent independently hydrogen, lower alkyl, lower alkanoyl or aroyl); when $R^2$ is a substituent on the 1-position, X represents N or CH, and $R^2$ represents hydrogen, substituted or unsubstituted lower alkyl, substituted or unsubstituted aryl, substituted or unsubstituted aralkyl or lower alkoxycarbonyl; when $R^2$ is a substituent on the 2-position, X represents N, and $R^2$ represents —$CR^5R^6R^7$ (in which $R^5$ represents substituted or unsubstituted lower alkyl; and $R^6$ and $R^7$ represent independently hydrogen or lower alkyl), substituted or unsubstituted aryl, substituted or unsubstituted aralkyl or lower alkoxycarbonyl; Y represents O or S; Q represents —$CR^8R^9CR^{10}R^{11}$— —$(CH_2)_n$— or —$CR^8$=$CR^9$—$(CH_2)_n$— (in which $R^8$, $R^9$, $R^{10}$ and $R^{11}$ represent independently hydrogen, substituted or unsubstituted lower alkyl, substituted or unsubstituted aryl, substituted or unsubstituted aralkyl or lower alkoxycarbonyl; and n is an integer of 0 to 2) [which are hereinafter referred to as Compounds (I), and the same applies to the compounds of other formula numbers] or pharmaceutically acceptable salts thereof.

In the definitions of the groups in Formula (I), the lower alkyl moiety of the lower alkyl, the lower alkanoyl and the lower alkoxycarbonyl means a straight-chain or branched alkyl group having 1 to 6 carbon atoms, such as methyl, ethyl, propyl, isopropyl, butyl, isobutyl, sec-butyl, tert-butyl, pentyl, neopentyl and hexyl. The aryl moiety of the aryl and the aroyl means a group such as phenyl and naphthyl. The aralkyl means an aralkyl group having 7 to 10 carbon atoms, such as benzyl and phenethyl. The halogen includes fluorin, chlorine, bromine and iodine. The substituted lower alkyl, the substituted aryl and the substituted aralkyl each has 1 to 3 independently-selected substituents, such as halogen, carboxyl and lower alkoxycarbonyl. The halogen and the lower alkyl moiety of the lower alkoxycarbonyl have the same meanings as defined above.

The pharmaceutically acceptable salts of Compounds (I) include acid addition salts and amino acid addition salts. Examples of the acid addition salts are inorganic acid addition salts such as hydrochloride and sulfate, and organic acid addition salts such as fumarate, tartrate, and citrate. Examples of the amino acid addition salts are salts with lysine, glycine and phenylalanine.

Compounds (I) in which $R^2$ is hydrogen can be usually present as Compounds (I-1) and Compounds (I-2) which are tautomers. Compounds (I-2) are also included in the present invention, which are hereinafter shown as Compounds (I-1).

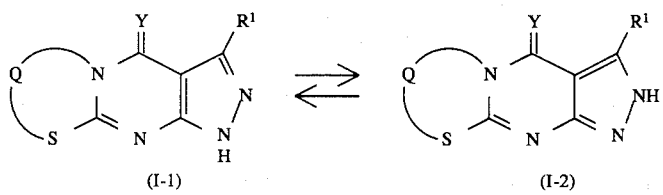

The processes for preparing Compounds (I) are described below.

In the processes shown below, if the defined groups are converted under the conditions of the processes or are not suitable for carrying out the processes, the processes can be readily carried out by applying thereto means conventionally used in organic synthetic chemistry, for example, protection or deprotection of functional groups.

Process 1

Compound (Ia), i.e., Compound (i) in which X is N, Y is O, and $R^1$ is hydrogen, can be prepared according to the following steps:

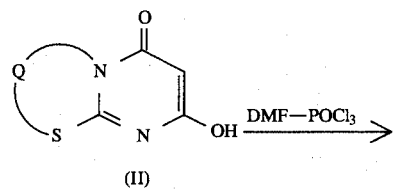

-continued

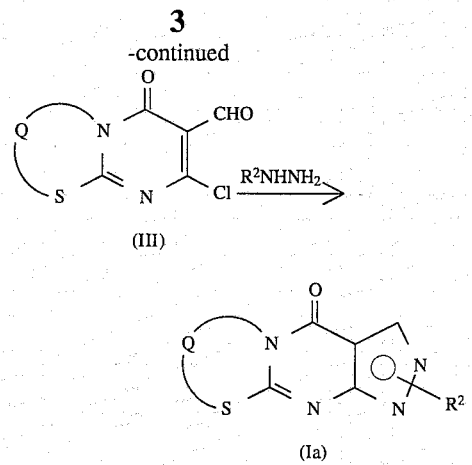

(In the formulae, $R^2$ and Q have the same meanings as defined above.)

Compound (III) can be obtained by reacting Compound (II) with 1 to 5 equivalents of dimethylformamide in phosphorus oxychloride at room temperature to 100° C. for 30 minutes to 3 hours.

Compound (Ia) can be obtained by reacting Compound (III) with 2 to 5 equivalents of hydrazine in an inert solvent such as alcohol (e.g., methanol, ethanol and propanol), toluene or xylene, at room temperature to 140° C. for 1 to 10 hours.

The starting compound (II) can be synthesized according to the known methods [J. Am. Chem. Soc., 64, 2709 (1942); Zh. Org. Khim., 11, 2200 (1975)] or similar methods.

Process 2

Compound (Ib), i.e., Compound (I) in which X is N, Y is O, and $R^1$ is substituted or unsubstituted lower alkyl, substituted or unsubstituted aryl, or substituted or unsubstituted aralkyl, can be prepared according to the following steps:

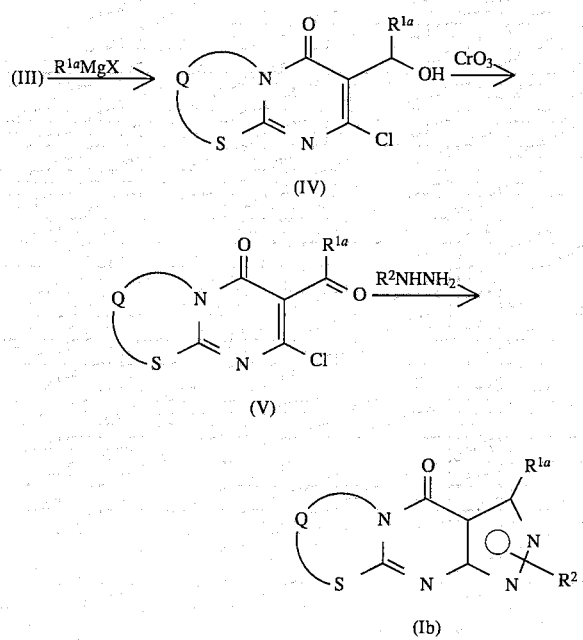

(In the formulae, $R^2$ and Q have the same meanings as defined above; and $R^{1a}$ represents substituted or unsubstituted lower alkyl, substituted or unsubstituted aryl, or substituted or unsubstituted aralkyl.)

Compound (IV) can be obtained by reacting Compound (III) with 1 to 5 equivalents of the Grignard reagent in an inert solvent (e.g., ether and tetrahydrofuran) at 0° to 60° C. for 1 to 10 hours.

Compound (V) can be obtained by reacting Compound (IV) with 1 to 5 equivalents of Jones' reagent (chromium oxide-sulfuric acid) in acetone at 0° C. to room temperature for 1 to 10 hours.

Compound (Ib) can be obtained by reacting Compound (V) with 2 to 5 equivalents of hydrazine in an inert solvent such as alcohol (e.g., methanol, ethanol and propanol), toluene or xylene, at room temperature to 140° C. for 1 to 10 hours.

Process 3

Compound (Ic), i.e., Compound (I) in which X is N, Y is O, and $R^1$ is amino, can be prepared according to the following steps:

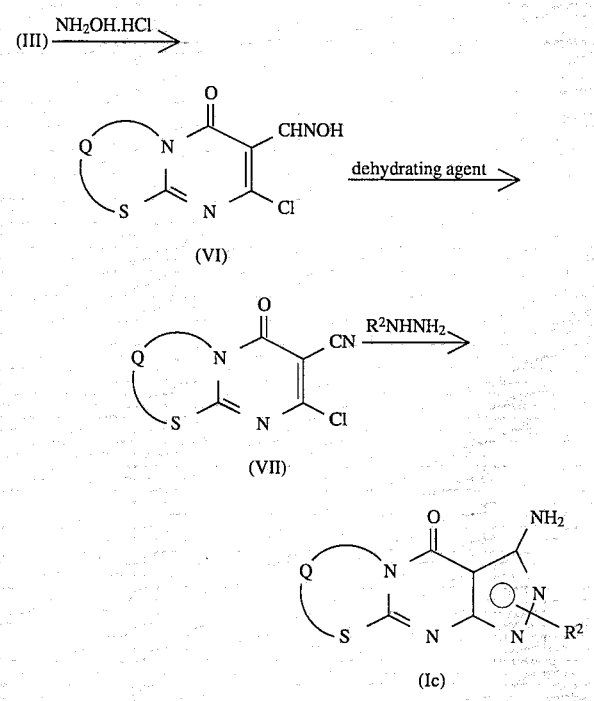

(In the formulae, $R^2$ and Q have the same meanings as defined above.)

Compound (VI) can be obtained by reacting Compound (III) with 1 to 5 equivalents of hydroxylamine hydrochloride in an inert solvent such as alcohol (e.g., methanol and ethanol) at room temperature to 50° C. for 5 minutes to 3 hours.

Compound (VII) can be obtained by treating Compound (VI) with a dehydrating agent (e.g., phosphorus oxychloride, thionyl chloride, acetic anhydride, phosphorus pentachloride and phosphorus pentaoxide) in an inert solvent (e.g., ether and tetrahydrofuran) or in the absence of a solvent at room temperature to 100° C. for 30 minutes to 5 hours.

Compound (Ic) can be obtained by reacting Compound (VII) with 2 to 5 equivalents of hydrazine in an inert solvent such as alcohol (e.g., methanol and ethanol), toluene or xylene, at room temperature to 140° C. for 1 to 10 hours.

Process 4

Compound (Id), i.e., Compound (I) in which X is N, Y is O, and $R^1$ is lower alkanoylamino or aroylamino, can be prepared according to the following step:

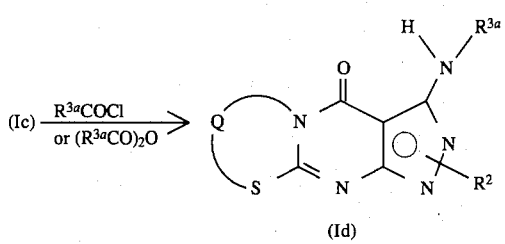

(In the formulae, $R^2$ and Q have the same meanings as defined above; and $R^{3a}$ represents lower alkanoyl or aroyl.)

Compound (Id) can be obtained by reacting Compound (Ic) with an equivalent of acid chloride or acid anhydride in pyridine, or in methylene chloride in the presence of a base such as triethylamine, at 0° to 60° C. for 1 to 10 hours.

Process 5

Compound (Ie), i.e., Compound (I) in which X is N, Y is O, and $R^1$ is —$NR^3R^{4a}$ (in which $R^3$ has the same meaning as defined above; and $R^{4a}$ represents lower alkyl), can be prepared according to the following step:

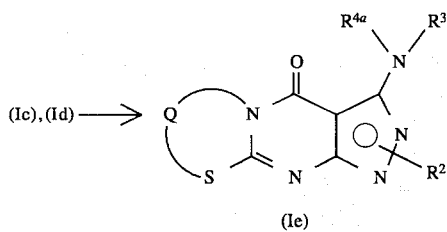

(in the formula $R^2$, $R^3$, $R^{4a}$ and Q have the same meanings as defined above.)

Compound (Ie) can be obtained by treating Compound (Ic) or Compound (Id) with 1 to 10 equivalents of alkyl halide (e.g., methyl iodide and ethyl iodide) in an inert solvent (e.g., dimethylformamide and dioxane) in the presence of a base (e.g., potassium carbonate and sodium hydride) at room temperature to 100° C. for 30 minutes to 24 hours.

Process 6

Compound (If), i.e., Compound (I) in which X is N, Y is O, and $R^1$ is lower alkylamino, can be prepared according to the following step:

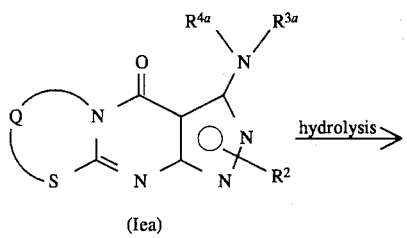

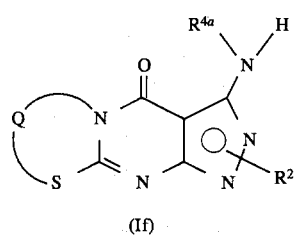

(In the formulae, $R^2$, $R^{3a}$, $R^{4a}$ and Q have the same meanings as defined above.)

Compound (If) can be obtained by subjecting Compound (Iea), i.e., Compound (Ie) in which $R^3$ is lower alkanoyl or aroyl, to reaction under the acidic condition where hydrochloric acid or the like is used, in a mixed solvent of dioxane and water at room temperature to 100° C. for 30 minutes to 12 hours.

Process 7

Compound (Ig), i.e., Compound (i) in which X is N, Y is O, and $R^1$ is halogen, can be prepared according to the following step:

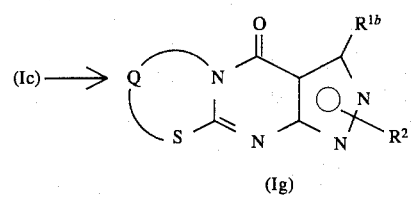

(In the formula, $R^2$ and Q have the same meanings as defined above; and $R^{1b}$ represents halogen.)

Compound (Ig) can be obtained by dissolving Compound (Ic) in an aqueous solution of hydrochloric acid, hydrogen bromide or the like, adding an equivalent of sodium nitrite at 0° C. to convert Compound (Ic) to a diazonium salt, and then reacting the salt with 1 to 5 equivalents of cuprous halide (e.g., cuprous chloride and cuprous bromide) at 0° C. to room temperature for 30 minutes to 2 hours.

Process 8

Compound (Ih), i.e., Compound (I) in which X is N, Y is O, and $R^2$ is hydrogen, can be prepared according to the following step:

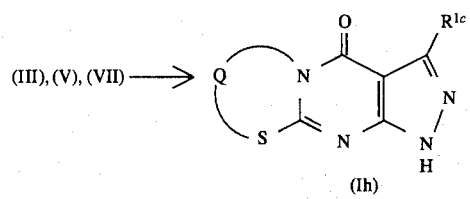

(In the formula, Q has the same meaning as defined above; and $R^{1c}$ represents hydrogen, substituted or unsubstituted lower alkyl, substituted or unsubstituted aryl, substituted or unsubstituted aralkyl or amino.)

Compound (Ih) can be obtained by heating a compound obtained by reacting Compound (III), (V) or (VII) with tert-butyl carbazate without isolation or purification, or by treating the said compound with a large excess of trifluoroacetic acid-hydrochloric acid at room temperature to 100° C. for 30 minutes to 5 hours.

Process 9

Compound (Ii), i.e., Compound (I) in which X is N, Y is O, and $R^2$ is a group other than hydrogen, can be prepared from Compound (Ih), in which $R^2$ is hydrogen, according to the following step:

(Ih) →

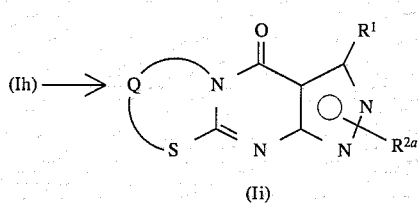

(Ii)

(In the formula, $R^1$ and Q have the same meanings as defined above; and $R^{2a}$ has the same meaning as $R^2$ except hydrogen.).

Compound (Ii) can be obtained by reacting Compound (Ih) with 1 to 10 equivalents of alkyl halide (e.g., methyl iodide, ethyl iodide, propyl iodide, isopropyl iodide, butyl iodide and butyl bromide), aralkyl halide (e.g., benzyl iodide and benzyl bromide), alkyl halogenoformate (e.g., methyl chloroformate and ethyl chloroformate), or halogenated fatty acid alkyl ester (e.g., tert-butyl bromoacetate), in the presence of a base (e.g., potassium carbonate, sodium carbonate, triethylamine and sodium hydride) in an inert solvent (e.g., dimethylformamide, dimethylacetamide, dioxane and acetone) at room temperature to 100° C. for 30 minutes to 24 hours.

Process 10

Compound (Ij), i.e., Compound (I) in which X is CH, Y is O, and $R^1$ is hydrogen, can be prepared according to the following steps:

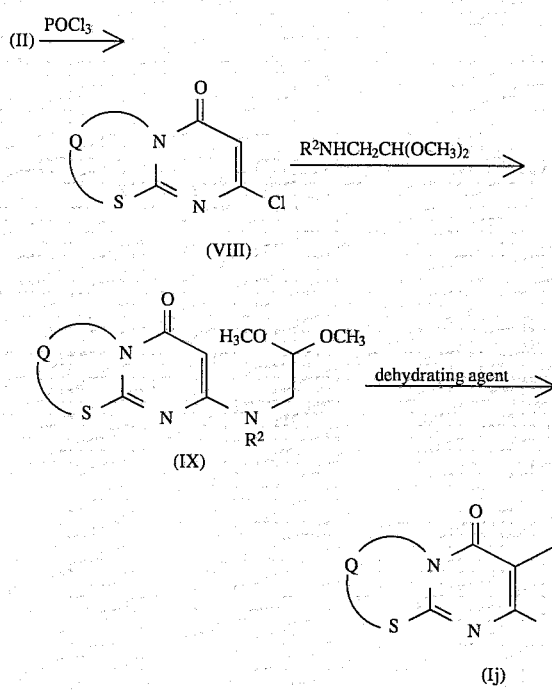

(In the formulae, $R^2$ and Q have the same meanings as defined above.)

Compound (VIII) can be obtained by treating Compound (II) with phosphorus oxychloride at room temperature to 100° C. for 30 minutes to 5 hours.

Compound (IX) can be obtained by reacting Compound (VIII) with 1 to 5 equivalents of an aminoacetaldehyde dimethylacetal derivative, in the presence of a base (e.g., triethylamine) in an alcohol (e.g., methanol, ethanol and propanol) at room temperature to 100° C. for 30 minutes to 10 hours.

Compound (Ij) can be obtained by treating Compound (IX) with a dehydrating agent (e.g., methanesulfonic acid, polyphosphoric acid and sulfuric acid) at room temperature to 120° C. for 30 minutes to 24 hours.

Process 11

Compound (Ik), i.e., Compound (I) in which Y is S, can be prepared according to the following step:

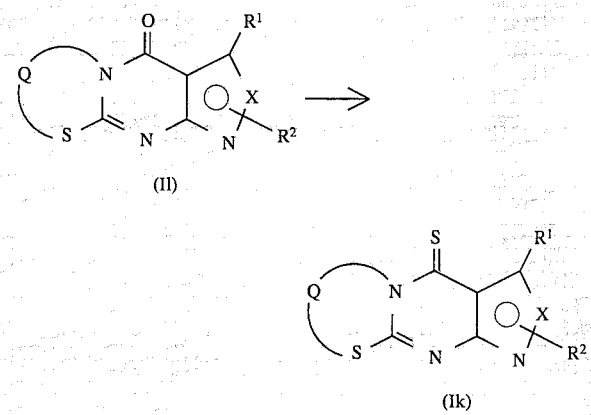

(In the formulae, $R^1$, $R^2$, X and Q have the same meanings as defined above.)

Compound (Ik) can be obtained by treating Compound (I) with 1 to 5 equivalents of diphosphorus pentasulfide or Lawesson's reagent at room temperature to 100° C. for 30 minutes to 10 hours. As a reaction solvent, when Lawesson's reagent is used, toluene, xylene, or the like is used, and when diphosphorus pentasulfide is used, pyridine or the like is used.

Process 12

Compound (Im), i.e., Compound (I) in which X is N, Y is O, and Q is —$CR^8R^9CR^{10}R^{11}$—$(CH_2)_n$— (wherein $R^8$, $R^9$, $R^{10}$, $R^{11}$ and n have the same meanings as defined above), can be prepared according to the following step:

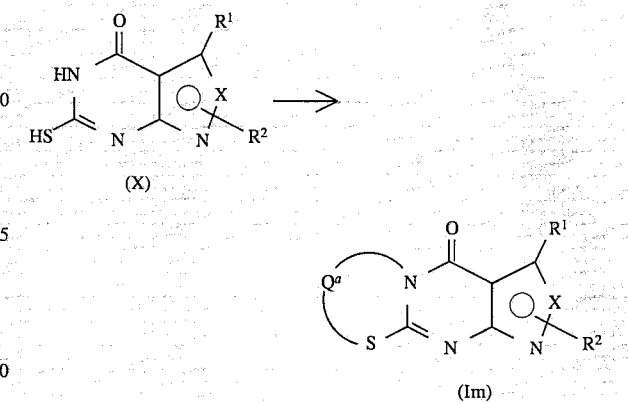

[In the formulae, $R^1$, $R^2$ and X have the same meanings as defined above; and $Q^a$ represents —$CR^8R^9CR^{10}R^{11}$— $(CH_2)_n$— (wherein $R^8$, $R^9$, $R^{10}$, $R^{11}$ and n have the same meanings as defined above).]

Compound (Im) can be obtained by reacting Compound (X) with 1 to 10 equivalents of alkyl dihalide (e.g., dibromoethane, dibromopropane and dibromobutane ) in the presence of a base (e.g., potassium carbonate, sodium carbonate, triethylamine and sodium hydride) in an inert solvent (e.g., dimethylformamide, dimethylacetamide, dioxane and acetone) at room temperature to 100° C. for 30 minutes to 24 hours.

The starting compound (X) wherein X is N can be synthesized according to the known method [Helv. Chim. Acta, 42, 349 (1959)].

Process 13

Compound (In), i.e., Compound (I) in which X is N, Y is O, and Q is —$CR^8R^9CR^{10}CH_3$—, can be prepared according to the following steps:

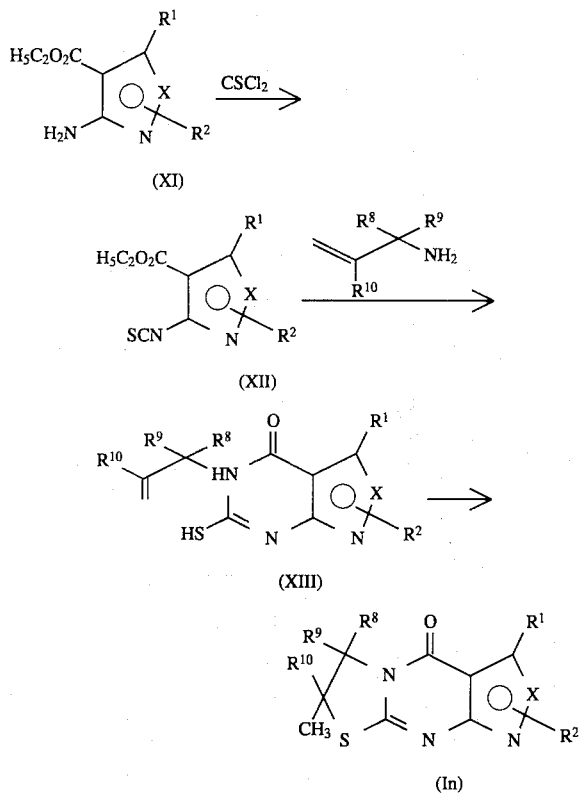

(In the formulae, $R^1$, $R^2$, $R^8$, $R^9$ and $R^{10}$ have the same meanings as defined above.)

Compound (XII) can be obtained by reacting Compound (XI) with 1 to 10 equivalents of thiophosgene in an inert solvent (e.g., methylene chloride and chloroform) at room temperature to 80° C. for 30 minutes to 24 hours.

Compound (XIII) can be obtained by reacting Compound (XII) with 1 to 10 equivalents of an allylamine derivative in an inert solvent (e.g., methylene chloride, toluene and ether) at room temperature to 100° C. for 30 minutes to 24 hours.

Compound (In) can be obtained by treating Compound (XIII) with acetic acid containing hydrogen chloride at room temperature to 100° C. for 30 minutes to 24 hours.

The starting compound (XI) wherein X is N can be synthesized according to the known method [Helv. Chim. Acta, 42, 349 (1959)].

Process 14

Compound (Io), i.e., Compound (i) in which X is N, Y is O, and Q is —$CR^8R^9CR^{10}R^{11}$—, can be alternatively prepared according to the following steps:

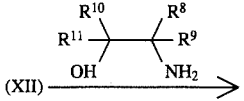

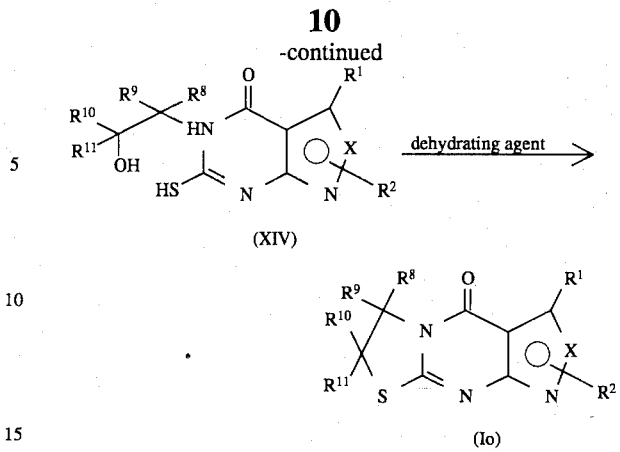

(In the formulae, $R^1$, $R^2$, $R^8$, $R^9$, $R^{10}$ and $R^{11}$ have the same meanings as defined above.)

Compound (XIV) can be obtained by treating Compound (XII) with 1 to 10 equivalents of an aminoethanol derivative in an inert solvent (e.g., methylene chloride, toluene and ether) at room temperature to 100° C. for 30 minutes to 24 hours.

Compound (Io) can be obtained by treating Compound (XIV) with a dehydrating agent (e.g., methanesulfonic acid, polyphosphoric acid and sulfuric acid) at room temperature to 120° C. for 30 minutes to 24 hours.

Process 15

Compound (Io) can be alternatively prepared according to the following step:

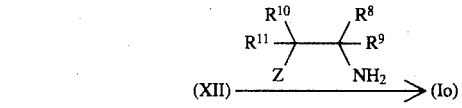

(In the formula, $R^1$, $R^2$, $R^8$, $R^9$, $R^{10}$ and $R^{11}$ have the same meanings as defined above; and Z represents a halogen atom.)

Compound (Io) can be obtained by reacting Compound (XII) with 1 to 10 equivalents of an aminoethyl halide derivative in an inert solvent (e.g., methylene chloride and chloroform) at room temperature to 100° C. for 30 minutes to 24 hours.

The intermediates and the desired compounds in the processes described above can be isolated and purified by purification methods conventionally used in organic synthetic chemistry, for example, filtration, extraction, washing, drying, concentration, recrystallization, and various kinds of chromatography. The intermediates may also be subjected to the subsequent reaction without purification.

In the case where a salt of Compound (I) is desired and it is produced in the form of the desired salt, it can be subjected to purification as such. In the case where Compound (I) is produced in the free state and its salt is desired, Compound (I) is dissolved or suspended in a suitable solvent, followed by addition of an acid or an amino acid to form a salt.

Compounds (I) and pharmaceutically acceptable salts thereof may be in the form of adducts with water or various solvents, which are also within the scope of the present invention.

Examples of Compounds (I) obtained in each process are shown in Table 1 below.

TABLE 1

| Compound No. | Example No. | R¹ | R² | X | Y | Q |
|---|---|---|---|---|---|---|
| 1 | 1 | H | 1-H | N | O | $CH_2CH_2$ |
| 2 | 2 | H | 1-$CH_3$ | N | O | $CH_2CH_2$ |
| 3 | 3 | H | 1-$C_6H_5$ | N | O | $CH_2CH_2$ |
| 4 | 3 | H | 2-$C_6H_5$ | N | O | $CH_2CH_2$ |
| 5 | 4 | H | 1-$CH_2C_6H_5$ | N | O | $CH_2CH_2$ |
| 6 | 5 | H | 1-$C(CH_3)_3$ | N | O | $CH_2CH_2$ |
| 7 | 5 | H | 2-$C(CH_3)_3$ | N | O | $CH_2CH_2$ |
| 8 | 6 | H | 1-$CH_2CF_3$ | N | O | $CH_2CH_2$ |
| 9 | 6 | H | 2-$CH_2CF_3$ | N | O | $CH_2CH_2$ |
| 10 | 7 | $CH_3$ | 1-$CH_3$ | N | O | $CH_2CH_2$ |
| 11 | 8 | 4-Cl—$C_6H_5$ | 1-$CH_3$ | N | O | $CH_2CH_2$ |
| 12 | 9 | $NH_2$ | 1-H | N | O | $CH_2CH_2$ |
| 13 | 10 | $NH_2$ | 1-$CH_3$ | N | O | $CH_2CH_2$ |
| 14 | 11 | $NH_2$ | 1-$C_6H_5$ | N | O | $CH_2CH_2$ |
| 15 | 11 | $NH_2$ | 2-$C_6H_5$ | N | O | $CH_2CH_2$ |
| 16 | 12 | $NH_2$ | 1-$CH_2C_6H_5$ | N | O | $CH_2CH_2$ |
| 17 | 13 | $NH_2$ | 2-$C(CH_3)_3$ | N | O | $CH_2CH_2$ |
| 18 | 14 | $NH_2$ | 2-$CH_2CF_3$ | N | O | $CH_2CH_2$ |
| 19 | 15 | $NH_2$ | 2-$CO_2CH_3$ | N | O | $CH_2CH_2$ |
| 20 | 16 | $NHCOCH_3$ | 1-$CH_3$ | N | O | $CH_2CH_2$ |
| 21 | 17 | $NHCOC_6H_5$ | 1-$CH_3$ | N | O | $CH_2CH_2$ |
| 22 | 18 | $NCH_3COCH_3$ | 1-$CH_3$ | N | O | $CH_2CH_2$ |
| 23 | 19 | $NHCH_3$ | 1-$CH_3$ | N | O | $CH_2CH_2$ |
| 24 | 20 | Cl | 1-$CH_3$ | N | O | $CH_2CH_2$ |
| 25 | 21 | Br | 1-$CH_3$ | N | O | $CH_2CH_2$ |
| 26 | 22 | H | 1-$CH_3CH_2$ | N | O | $CH_2CH_2$ |
| 27 | 22 | H | 2-$CH_3CH_2$ | N | O | $CH_2CH_2$ |
| 28 | 23 | H | 1-$CH_3(CH_2)_2$ | N | O | $CH_2CH_2$ |
| 29 | 23 | H | 2-$CH_3(CH_2)_2$ | N | O | $CH_2CH_2$ |
| 30 | 24 | H | 1-$CH(CH_3)_2$ | N | O | $CH_2CH_2$ |
| 31 | 24 | H | 2-$CH(CH_3)_2$ | N | O | $CH_2CH_2$ |
| 32 | 25 | H | 1-$CH_3(CH_2)_3$ | N | O | $CH_2CH_2$ |
| 33 | 25 | H | 2-$CH_3(CH_2)_3$ | N | O | $CH_2CH_2$ |
| 34 | 26 | H | 1-$CH_2CO_2C(CH_3)_3$ | N | O | $CH_2CH_2$ |
| 35 | 26 | H | 2-$CH_2CO_2C(CH_3)_3$ | N | O | $CH_2CH_2$ |
| 36 | 27 | H | 1-$CH_2CO_2H$ | N | O | $CH_2CH_2$ |
| 37 | 28 | H | 2-$CH_2CO_2H$ | N | O | $CH_2CH_2$ |
| 38 | 29 | H | 1-$CH_3$ | CH | O | $CH_2CH_2$ |
| 39 | 30 | H | 1-$CH_3$ | N | S | $CH_2CH_2$ |
| 40 | 31 | H | 1-$CH_3$ | N | O | $CHCH_3CH_2$ |
| 41 | 32 | H | 1-$CH_3$ | N | O | $CHCH_3CHCH_3$ |
| 42 | 33 | H | 1-$CH_3$ | N | O | $CH_2CHCO_2CH_2CH_3$ |
| 43 | 34 | H | 1-$CH_3$ | N | O | $CH_2CHCOOH$ |
| 44 | 35 | H | 1-$CH_3$ | N | O | $CH_2CH_2CH_2$ |
| 45 | 36 | H | 1-$CH_3$ | N | O | $CH_2CH_2CH_2CH_2$ |
| 46 | 37 | H | 1-$CH_3$ | N | O | $CH_2CHCH_3$ |
| 47 | 38 | H | 1-$CH_3$ | N | O | $CH_2C(CH_3)_2$ |
| 48 | 39 | H | 1-$CH_3$ | N | O | $C(CH_3)_2CH_2$ |
| 49 | 40 | H | 1-$CH_3$ | N | O | $CHC_6H_5CHC_6H_5$ |
| 50 | 41 | H | 1-$CH_3$ | N | O | $CH_2CHC_6H_5$ |
| 51 | 42 | H | 1-$CH_3$ | N | O | $CH=CH$ |

The pharmacological activities of representative Compounds (I) are shown below by test examples.

Test Example 1

Anti-inflammatory Activity

The experiment was carried out by using groups of Wister rats (male; 150 g), each group consisting of five rats. The right hind-limb paw volume of a rat was measured using a plethysmograph (Unicom Co., Ltd.; TK-101).

To the right hind-limb paw was subcutaneously injected 0.1 ml of 1% carrageenin or 1% zymosan as an inflammation inductive agent. The right hind-limb paw volume was measured 3 hours after the injection of carrageenin or 4 hours after the injection of zymosan. The swelling rate was determined by comparing the right hind-limb paw volume before the injection of the inductive agent with that after the injection according to the following equation:

$$\text{Carrageenin-induced swelling rate (\%)} = \frac{V_1 - V_0}{V_0} \times 100$$

$V_1$: The right hind-limb paw volume 3 hours after the administration of carrageenin.

$V_0$: The right hind-limb paw volume before the administration of carrageenin.

$$\text{Zymosan-induced swelling rate (\%)} = \frac{V_1 - V_0}{V_0} \times 100$$

$V_1$: The right hind-limb paw volume 4 hours after the administration of zymosan.

$V_0$: The right hind-limb paw volume before the administration of zymosan.

The test compounds were suspended in a 5% gum arabic solution, and orally administered one hour before the administration of the inductive agent.

On the other hand, only a 5% gum arabic solution was orally administered to the control group.

The suppression rate (%) was determined by comparing the test compound-administered group with the control group according to the following equation:

Suppression rate (%) =

$$\frac{\text{Swelling rate of control group} - \text{Swelling rate of test compound-administered group}}{\text{Swelling rate of control group}} \times 100$$

The results of the tests are shown in Tables 2 and 3.

TABLE 2

| Compound No. | Dose (mg/kg) | Carrageenin-induced swelling rate (%) | Suppression rate (%) |
| --- | --- | --- | --- |
| 2 | 25 | 43.0 | 27.8 |
| Control | — | 59.6 | — |
| 40 | 100 | 35.3 | 44.8 |
| 46 | 100 | 39.6 | 38.1 |
| Control | — | 64.0 | — |

TABLE 3

| Compound No. | Dose (mg/kg) | Zymosan-induced swelling rate (%) | Suppression rate (%) |
| --- | --- | --- | --- |
| 2 | 25 | 45.4 | 26.8 |
| Control | — | 62.0 | — |
| 10 | 100 | 22.1 | 51.9 |
| 40 | 100 | 25.9 | 43.6 |
| Control | — | 45.9 | — |

Test Example 2

Effect on Delayed Type Hypersensitivity (DTH)

The experiment was carried out by using groups of 7-weeks-old BALB/C-strain mice, each group consisting of six mice. The mice were sensitized by the subcutaneous injection of 1×10⁸ cells/0.1 ml of sheep red blood cells (SRBC; Japan Biotest Co., Ltd.). After 4 days, 1×10⁸ cells/0.025 ml of SRBC was subcutaneously injected into the right hind-limb paw, whereas 0.025 ml of physiological saline was subcutaneously injected into the left hind-limb paw. The swelling of both paws was measured using Dial Thickness Gauge (Peacock Co., Ltd.) 24 hours after the injection. The edema (mm) was defined as the difference in swelling between the SRBC-injected paw and the physiological saline-injected paw. The test compounds were suspended in a 5% gum arabic solution, and orally administered twice after the sensitization, i.e., one hour before and 6 hours after the administration of SRBC.

Only a 5% gum arabic solution was orally administered to the control group.

The suppression rate (%) was determined by comparing the test compound-administered group with the control group according to the following equation:

Suppression rate (%) =

$$\frac{\text{Edema of control group} - \text{Edema of test compound-administered group}}{\text{Edema of control group}} \times 100$$

The results of the tests are shown in Table 4.

TABLE 4

| Compound No. | Dose (mg/kg) | Suppression rate (%) |
| --- | --- | --- |
| 2 | 100 | 35.0 |
| 44 | 100 | 32.6 |
| 45 | 100 | 50.3 |
| 51 | 100 | 37.0 |

Test Example 3

Analgesic Activity (Acetic Acid-Induced Writhing Method)

The experiment was carried out by using groups of male ddy-strain mice weighing 18±1 g, each group consisting of five mice. The mice received intraperitoneal injection of 0.1 ml/10 g. of 0.7% acetic acid. The frequency of writhing syndrome was counted for 5 minutes from 10 minutes after the injection of acetic acid and the suppression rate against the control group was determined. The test compound was orally administered to the mice one hour before the injection of acetic acid.

Suppression rate (%) =

$$\frac{\text{Writhing frequency of control group} - \text{Writhing frequency of test compound-administered group}}{\text{Writhing frequency of control group}} \times 100$$

The results of the tests are shown in Table 5.

TABLE 5

| Compound No. | Dose (mg/kg) | Writhing frequency | Suppression rate (%) |
| --- | --- | --- | --- |
| 2 | 1 | 9.8 | 44.3 |
|  | 3 | 6.4 | 63.6 |
|  | 10 | 4.8 | 72.7 |
|  | 30 | 0.8 | 53.4 |
| Control | — | 17.6 | — |

Test Example 4

Anti-ulcer Activity in Water Immersion Restraint-Induced Stress Ulcer Model

Donryu-strain male rats weighing 190 to 210 g (test compound-administered groups each consisting of five rats and control groups each consisting of five rats) were fasted for 17 hours. Each test compound was suspended in a 50% aqueous solution of Polyethylene Glycol 400 and orally administered to the rats. The rats were immersed in a water-bath at 21°±1° C. using a stress cage (Tokyo University Pharmaceutical Department Type) to the sword-like protrusion 30 minutes after the administration, and were subjected to stress for 7 hours. After the stressing, the rats were sacrificed with $CO_2$ and their stomachs were excised. The length of spotty and linear erosions and ulcers was measured using a binocular microscope (x5), and the total length was defined as the ulcer index of each animal.

The suppression rate was determined by comparing the test compound-administered group with the control group according to the following equation:

Suppression rate (%) =

$$\frac{\text{Total length} - \text{Total length of ulcers}}{\text{of ulcers of}} \times 100$$
$$\frac{\text{control group}}{\text{Total length of ulcers}} \times 100$$
$$\text{of control group}$$

A 50% aqueous solution of Polyethylene Glycol 400 was administered to the control group at a dose of 5 ml/kg. The results of the tests are shown in Table 6.

TABLE 6

| Compound No. | Dose (mg/kg, p.o.) | Ulcer index (mm) | Suppression rate (%) |
|---|---|---|---|
| 32 | 30 | 2.8 ± 1.4 | 86 |
| Control | — | 19.6 ± 2.2 | — |
| 30 | 10 | 10.6 ± 2.3 | 57 |
|  | 30 | 7.6 ± 2.8 | 69 |
| Control | — | 24.6 ± 2.7 | — |
| 44 | 3 | 15.2 ± 2.1 | 38 |
|  | 10 | 8.6 ± 2.7 | 65 |
|  | 30 | 5.0 ± 3.2 | 80 |
| Control | — | 24.6 ± 2.7 | — |

Compounds (I) and pharmaceutically acceptable salts thereof can be administered as they are, or in the form of various pharmaceutical compositions. The pharmaceutical compositions in accordance with the present invention can be prepared by uniformly mixing an effective amount of Compound (I) or a pharmaceutically acceptable salt thereof, as an active ingredient, with a pharmaceutically acceptable carrier. It is desired that such pharmaceutical compositions are prepared in a unit dose form suitable for oral administration.

For preparing a pharmaceutical composition for oral administration, any useful pharmaceutically acceptable carrier can be used. For example, liquid preparations for oral administration such as suspension and syrup can be prepared using water, sugars such as sucrose, sorbitol and fructose, glycols such as polyethylene glycol and propylene glycol, oils such as sesame oil, olive oil and soybean oil, preservatives such as p-hydroxybenzoates, flavors such as strawberry flavor and peppermint, and the like. Powders, pills, capsules and tablets can be prepared using excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid esters, plasticizers such as glycerin, and the like. Tablets and capsules are the most useful oral unit dose forms because of the readiness of administration. For preparing tablets and capsules, solid pharmaceutical carriers are used.

The effective dose and the administration schedule of Compounds (I) and pharmaceutically acceptable salts thereof vary depending upon the mode of administration, the age, body weight and conditions of a patient, etc. However, it is generally preferred to administer Compound (I) or a pharmaceutically acceptable salt thereof in a daily dose of 1 to 100 mg/kg in 3 to 4 parts.

Certain embodiments of the invention are illustrated in the following Examples, Reference Examples and Preparation Examples.

BEST MODE FOR CARRYING OUT THE INVENTION

EXAMPLE 1

6,7-Dihydropyrazolo[3,4-d]thiazolo[3,2-a]pyrimidin-4(1H)-one (Compound 1)

In 100 ml of propanol was dissolved 2.5 g (11.5 mmol) of the compound prepared in Reference Example 1, and 3.05 g (23.1 mmol) of tert-butyl carbazate was added to the solution, followed by heating under reflux for 3 hours. After cooling, the solvent was evaporated and chloroform was added. The precipitated crystals were collected by filtration, washed with water, and then recrystallized from dimethylformamide/water to give 1.33 g (59%) of Compound 1.

Melting Point: >300° C. Elemental Analysis (%): $C_7H_6N_4OS$ Calcd.: C, 43.29; H, 3.11; N, 28.85 Found: C, 43.55; H, 2.77; N, 28.83 IR(KBr) $cm^{-1}$: 3154, 1661, 1568, 943 NMR(DMSO-$d_6$) δ (ppm): 13.4(1H, brs), 8.13(1H, s), 4.45(2H, t, J=7 Hz), 3.62(2H, t, J=7 Hz) MS(m/e): 194($M^+$), 135

EXAMPLE 2

6,7-Dihydro-1-methylpyrazolo[3,4-d]thiazolo[3,2-a]pyrimidin-4(1H)-one (Compound 2)

In 60 ml of ethanol was dissolved 2.0 g (9.2 mmol) of the compound prepared in Reference Example 1, and 0.98 ml (18.5 mmol) of methylhydrazine was added to the solution, followed by stirring at room temperature for one hour. After the reaction was completed, the precipitated crystals were collected by filtration, washed with water, and then recrystallized from dimethylformamide/water to give 1.45 g (76%) of Compound 2.

Melting Point: 257°–258° C. Elemental Analysis (%): $C_8H_8N_4OS$ Calcd.: C, 46.14; H, 3.87; N, 26.91 Found: C, 46.07; H, 3.63; N, 26.64 IR(KBr) $cm^{-1}$: 1692, 1562, 1513 NMR(DMSO-$d_6$) δ (ppm): 7.95(1H, s), 4.38(2H, t, J=7 Hz), 3.84(3H, s), 3.58(2H, t, J=7 Hz) MS(m/e): 208($M^+$), 149

EXAMPLE 3

6,7-Dihydro-1-phenylpyrazolo[3,4-d]thiazolo[3,2-a]pyrimidin-4(1H)-one (Compound 3)

6,7-Dihydro-2-phenylpyrazolo[3,4-d]thiazolo[3,2-a]pyrimidin-4(2H)-one (Compound 4)

In 160 ml of xylene was dissolved 2.72 g (12.6 mmol) of the compound prepared in Reference Example 1, and 3.09 ml (31.4 mmol) of phenylhydrazine was added to the solution, followed by heating under reflux for 10 hours. After evaporation of the solvent, the residue was subjected to partition between chloroform and water, and the chloroform layer was concentrated to dryness under reduced pressure. The residue was subjected to silica gel column chromatography and eluted with chloroform-methanol (100:1). Then, the first and second main fractions were recrystallized from dimethylformamide/water to give 1.29 g (38%) of Compound 3 and 1.23 g (36%) of Compound 4, respectively.

Compound 3

Melting Point: 208.0°–209.0° C. Elemental Analysis (%): $C_{13}H_{10}N_4OS$ Calcd.: C, 57.76; H, 3.72; N, 20.72 Found: C, 57.84; H, 3.69; N, 20.59 IR(KBr) $cm^{-1}$: 1679, 1549, 1509 NMR(DMSO-$d_6$) δ (ppm): 8.28(1H, s), 8.04–7.34(5H, m), 4.40(2H, t, J=7 Hz), 3.60(2H, t, J=7 Hz) MS(m/e): 270($M^+$), 228

Compound 4

Melting Point: 164.0°–172.0° C. Elemental Analysis (%): $C_{13}H_{10}N_4OS$ Calcd.: C, 57.76; H, 3.72; N, 20.72 Found: C, 58.02; H, 3.58; N, 20.44 IR(KBr) $cm^{-1}$: 1691, 1580, 1464

NMR(DMSO-d$_6$) δ (ppm): 9.30(1H, s), 8.05–7.38(5H, m), 4.40(2H, t, J=7 Hz), 3.55(2H, t, J=7 Hz) MS(m/e): 270(M$^+$), 228

EXAMPLE 4

1-Benzyl-6,7-dihydropyrazolo[3,4-d]thiazolo[3,2-a]pyrimidin-4(1H)-one (Compound 5)

In 60 ml of propanol was dissolved 2.0 g (9.4 mmol) of the compound prepared in Reference Example 1, and 3.66 g (18.8 mmol) of benzylhydrazine dihydrochloride and 5 ml of triethylamine were added to the solution, followed by heating under reflux for 6 hours. After evaporation of the solvent, the residue was subjected to partition between chloroform and water, and the chloroform layer was concentrated to dryness under reduced pressure. The residue was subjected to silica gel column chromatography and eluted with chloroform. The main fraction was recrystallized from dimethylformamide/water to give 1.79 g (68%) of Compound 5.

Melting Point: 180.5°–182.0° C. Elemental Analysis (%): C$_{14}$H$_{12}$N$_4$OS Calcd.: C, 59.13 ; H, 4.25; N, 19.70 Found: C, 59.11; H, 4.31; N, 19.47 IR(KBr) cm$^{-1}$: 1713, 1547, 1285 NMR(CDCl$_3$) δ (ppm): 7.97(1H, s), 7.30(5H, brs), 5.40(2H, s), 4.46(2H, t, J=7 Hz), 3.47(2H, t, J=7 Hz) MS(m/e): 284(M$^+$), 207

EXAMPLE 5

1-tert-Butyl-6,7-dihydropyrazolo[3,4-d]thiazolo[3,2-a]pyrimidin-4(1H)-one (Compound 6)

2-tert-Butyl-6,7-dihydropyrazolo[3,4-d]thiazolo[3,2-a]pyrimidin-4(2H)-one (Compound 7)

In 3 ml of propanol was dissolved 0.2 g (0.94 mmol) of the compound prepared in Reference Example 1, and 0.23 g (1.87 mmol) of tert-butylhydrazine hydrochloride and 0.65 ml of triethylamine were added to the solution, followed by heating under reflux for 6 hours. After evaporation of the solvent, the residue was subjected to partition between chloroform and water, and the chloroform layer was concentrated to dryness under reduced pressure. The residue was subjected to silica gel column chromatography and eluted with chloroform-methanol (100:1). The first and second main fractions were recrystallized from dimethylformamide/water to give 1.29 g (38%) of Compound 6 and 1.23 g (36%) of Compound 7, respectively, in pure form.

Compound 6

Melting Point: 203.7°–204.4° C. Elemental Analysis (%): C$_{11}$H$_{14}$N$_4$OS Calcd.: C, 52.78; H., 5.63; N, 22.38 Found: C, 52.85; H, 5.81; N, 22.04 IR(KBr) cm$^{-1}$: 1673, 1561, 1549 NMR(CDCl$_3$) δ (ppm): 7.93(1H, s), 4.43(2H, t, J=7 Hz), 3.49(2H, t, J=7 Hz), 1.72(9H, s) MS(m/e): 250(M$^+$), 194

Compound 7

Melting Point: 166.4°–169.8° C. Elemental Analysis (%): C$_{11}$H$_{14}$N$_4$OS•0.4H$_2$O Calcd.: C, 51.30; H, 5.79; N, 21.76 Found: C, 51.31; H, 5.87; N, 21.68 IR(KBr) cm$^{-1}$: 1701, 1672, 1581 NMR(CDCl$_3$) δ (ppm): 8.10(1H, s), 4.45(2H, t, J=7 Hz), 3.44(2H, t, J=7 Hz), 1.65(9H, s) MS(m/e): 250(M$^+$), 194

EXAMPLE 6

6,7-Dihydro-1-(2,2,2-trifluoroethyl)pyrazolo[3,4-d]thiazolo[3,2-a]pyrimidin-4(1H)-one (Compound 8)

6,7-Dihydro-2-(2,2,2-trifluoroethyl)pyrazolo[3,4-d]thiazolo[3,2-a]pyrimidin-4(2H)-one (Compound 9)

In 100 ml of propanol was dissolved 1.91 g (8.13 mmol) of the compound prepared in Reference Example 1, and 3.5 ml (27.8 mmol) of 2,2,2-trifluoroethylhydrazine (70% aqueous solution) was added to the solution, followed by heating under reflux for 3 hours. After evaporation of the solvent, the residue was subjected to partition between chloroform and water, and the chloroform layer was concentrated to dryness under reduced pressure. The residue was subjected to silica gel column chromatography and eluted with chloroform-methanol (100:1). The first and second main fractions gave 0.62 g (26%) of Compound 8 and 1.05 g (43%) of Compound 9, respectively. Both compounds were recrystallized from ethanol for purification.

Compound 8

Melting Point: 227.2°–228.2° C. IR(KBr) cm$^{-1}$: 1697, 1589, 1472 NMR(CDCl$_3$) δ (ppm): 8.13(1H, s), 4.83(2H, q, J=8 Hz), 4.46(2H, t, J=7 Hz), 3.46(2H, t, J=7 Hz) MS(m/e): 276(M$^+$), 207

Compound 9

Melting Point: 183.3°–183.9° C. Elemental Analysis (%): C$_9$H$_7$F$_3$N$_4$OS Calcd.: C, 39.13; H, 2.55; N, 20.28 Found: C, 39.22; H, 2.23; N, 20.07 IR(KBr) cm$^{-1}$: 1712, 1550, 1506, 1177 NMR(CDCl$_3$) δ (ppm): 8.06(1H, s), 4.84(2H, q, J=8 Hz), 4.52(2H, t, J=7 Hz), 3.54(2H, t, J=7 Hz) MS(m/e): 276(M$^+$), 216

EXAMPLE 7

6,7-Dihydro-1,3-dimethylpyrazolo[3,4-d]thiazolo[3,2-a]pyrimidin-4(1H)-one (Compound 10)

In 35 ml of propanol was dissolved 1.20 g (5.2 mmol) of the compound prepared in Reference Example 5, and 0.55 ml (10.4 mmol) of methylhydrazine was added to the solution, followed by heating under reflux for 3 hours. After evaporation of the solvent, the residue was subjected to partition between chloroform and water, and the chloroform layer was concentrated to dryness under reduced pressure. The residue was subjected to silica gel column chromatography and eluted with chloroform to give 1.13 g (98%) of Compound 10. The compound was recrystallized from ethanol for purification.

Melting Point: 229.1°–229.8° C. Elemental Analysis (%): C$_9$H$_{10}$N$_4$OS Calcd.: C, 48.64; H, 4.53; N, 25.21 Found: C, 48.67; H, 4.25; N, 25.16 IR(KBr) cm$^{-1}$: 1694, 1556, 1519 NMR(CDCl$_3$) δ (ppm): 4.47(2H, t, J=7 Hz), 3.83(3H, s), 3.50(2H, t, J=7 Hz), 2.53(3H, s) MS(m/e): 222(M$^+$), 180

EXAMPLE 8

3-(4-Chlorophenyl)-6,7-dihydro-1-methylpyrazolo[3,4 -d]thiazolo[3,2-a]pyrimidin-4(1H)-one (Compound 11)

In 50 ml of ethanol was dissolved 1.53 g (4.68 mmol) of the compound prepared in Reference Example 7, and 0.50 ml (9.40 mmol) of methylhydrazine was added to the solution, followed by heating under reflux for 30 minutes. After cooling, the precipitated crystals were collected by filtration, and then washed with methanol. Recrystallization from chloroform/ethanol gave 1.37 g (92%) of Compound 11 in pure form.

Melting Point: 255.8°–256.8° C. Elemental Analysis (%): $C_{14}H_{11}ClN_4OS$ Calcd.: C, 52.75; H, 3.48; N, 17.58 Found: C, 52.94; H, 3.18; N, 17.57 IR(KBr) $cm^{-1}$: 1671, 1550, 1501 NMR(CDCl$_3$) δ (ppm): 8.31–8.26(2H, m), 7.43–7.38(2H, m), 4.51(2H, t, J=8 Hz), 3.94(3H, s), 3.52(2H, t, J=8 Hz) MS(m/e): 318($M^+$), 276

EXAMPLE 9

3-Amino-6,7-dihydropyrazolo[3,4-d]thiazolo[3,2 -a]pyrimidin-4(1H)-one (Compound 12)

In 70 ml of ethanol was dissolved 0.74 g (3.5 mmol) of the compound prepared in Reference Example 3, and 0.92 g (7.0 mmol) of tert-butyl carbazate was added to the solution, followed by heating under reflux for 3 hours. After evaporation of the solvent, the residue was subjected to partition between chloroform and water. The chloroform layer was concentrated to dryness under reduced pressure to give 3-amino-2-tert-butoxycarbonyl-6,7-dihydropyrazolo[3,4 -d]thiazolo[3,2-a]pyrimidin-4(2H)-one as a semi-oily substance. Without purification of this substance, 2N hydrochloric acid was added thereto, followed by heating under reflux for one hour. After evaporation of the solvent, the residue was washed with ethyl acetate and isopropanol to give 0.66 g (77%) of the hydrochloride of Compound 12.

Melting Point: >300° C. Elemental Analysis (%): $C_7H_7N_5OS \cdot HCl$ Calcd.: C, 34.22; H, 3.28; N, 28.51 Found: C, 34.26; H, 2.92; N, 28.31 IR(KBr) $cm^{-1}$: 3200, 1658, 1605, 1511 NMR(DMSO-d$_6$) δ (ppm): 7.53(4H, brs), 4.33(2H, t, J=8 Hz), 3.58(2H, t, J=8 Hz) MS(m/e): 209($M^+$), 167

EXAMPLE 10

3-Amino-6,7-dihydro-1-methylpyrazolo[3,4 -d]thiazolo[3,2-a]pyrimidin-4(1H)-one (Compound 13)

In 200 ml of ethanol was dissolved 2.13 g (10.0 mmol) of the compound prepared in Reference Example 3, and 1.06 ml (20 mmol) of methylhydrazine was added to the solution, followed by stirring at room temperature for 30 minutes. After evaporation of the solvent, the residue was washed with water, and then recrystallized from dimethylformamide/methanol to give 1.67 g (75%) of Compound 13.

Melting Point: 280°–283° C. Elemental Analysis (%): $C_8H_9N_5OS$ Calcd.: C, 43.04; H, 4.06; N, 31.37 Found: C, 43.34; H, 3.93; N, 31.24 IR(KBr) $cm^{-1}$: 3390, 1679, 1567 NMR(DMSO-d$_6$) δ (ppm): 5.25(2H, brs), 4.30(2H, t, J=8 Hz), 3.54(3H, s), 3.53(2H, t, J=8 Hz) MS(m/e): 223($M^+$), 181

EXAMPLE 11

3-Amino-6,7-dihydro-1-phenylpyrazolo[3,4 -d]thiazolo[3,2-a]pyrimidin-4(1H)-one (Compound 14)

3-Amino-6,7-dihydro-2-phenylpyrazolo[3,4 -d]thiazolo[3,2-a]pyrimidin-4(2H)-one (Compound 15)

In 250 ml of ethanol was dissolved 2.5 g (11.7 mmol) of the compound prepared in Reference Example 3, and 2.5 ml (25.4 mmol) of phenylhydrazine was added to the solution, followed by heating under reflux for 30 minutes. After evaporation of the solvent, the residue was subjected to partition between chloroform and water, and the chloroform layer was concentrated to dryness under reduced pressure. The residue was subjected to silica gel column chromatography and eluted with chloroform-methanol (50:1). The first and second main fractions were recrystallized from ethyl acetate and ethyl acetate/hexane, respectively, to give 0.48 g (15%) of Compound 14 and 2.40 g (75%) of Compound 15, respectively, in pure form.

Compound 14

Melting Point: 167.0°–168.0° C. Elemental Analysis (%): $C_{13}H_{11}N_5OS$ Calcd.: C, 54.73; H, 3.89; N, 24.55 Found: C, 54.64; H, 3.68; N, 24.50 IR(KBr) $cm^{-1}$: 3400, 1669, 1564 NMR(DMSO-d$_6$) δ (ppm): 7.96–7.92(2H, m), 7.49–7.43(2H, m), 7.27–7.20(1H, m), 5.62(2H, brs), 4.37(2H, t, J=8 Hz), 3.60(2H, t, J=8 Hz) MS(m/e): 285($M^+$), 243

Compound 15

Melting Point: 232.0°–232.5° C. Elemental Analysis (%): $C_{13}H_{11}N_5OS$ Calcd.: C, 54.73; H, 3.89; N, 24.55 Found: C, 54.43; H, 3.66; N, 24.43 IR(KBr) $cm^{-1}$: 3300, 1625, 1583 NMR(DMSO-d$_6$) δ (ppm): 7.60–7.34(5H, m), 6.41(2H, brs), 4.27(2H, t, J=7 Hz), 3.48(2H, t, J=7 Hz) MS(m/e): 285($M^+$), 243

EXAMPLE 12

3-Amino-1-benzyl-6,7-dihydropyrazolo[3,4 -d]thiazolo[3,2-a]pyrimidin-4(1H)-one (Compound 16)

In 60 ml of propanol was dissolved 2.0 g (9.4 mmol) of the compound prepared in Reference Example 3, and 2.9 g (14.8 mmol) of benzylhydrazine dihydrochloride and 4.6 ml of triethylamine were added to the solution, followed by heating under reflux for one hour. After evaporation of the solvent, the residue was subjected to partition between chloroform and water, and the chloroform layer was concentrated to dryness under reduced pressure. The residue was recrystallized from chloroform/ethanol to give 1.62 g (58%) of Compound 16 in pure form.

Melting Point: 233.0°–235.5° C. Elemental Analysis (%): $C_{14}H_{13}N_5OS \cdot 0.2H_2O$ Calcd.: C, 55.51; H, 4.46; N, 23.12 Found: C, 55.50; H, 4.17; N, 22.94 IR(KBr) $cm^{-1}$: 3462, 1681, 1547 NMR(DMSO-d$_6$) δ (ppm): 7.30–7.10(5H, m), 5.30(2H, brs), 5.12(2H, s), 4.30(2H, t, J=8 Hz), 3.50(2H, t, J=8 Hz) MS(m/e): 299($M^+$), 208

EXAMPLE 13

3-Amino-2-tert-butyl-6,7-dihydropyrazolo[3,4-d]thiazolo[3,2-a]pyrimidin-4(2H)-one (Compound 17)

In 3 ml of propanol was dissolved 0.2 g (0.94 mmol) of the compound prepared in Reference Example 3, and 0.23 g (1.87 mmol) of tert-butylhydrazine hydrochloride and 0.65 ml of triethylamine were added to the solution, followed by heating under reflux for 3 hours. After evaporation of the solvent, the residue was subjected to partition between chloroform and water, and the chloroform layer was concentrated to dryness under reduced pressure. The residue was subjected to silica gel column chromatography and eluted with chloroform-methanol (100:1). The main fraction was recrystallized from ethyl acetate to give 0.14 g (56%) of Compound 17 in pure form.

Melting Point: 154.5°–158.0° C. Elemental Analysis (%): $C_{11}H_{15}N_5OS$ Calcd.: C, 49.79; H, 5.69; N, 26.39 Found: C, 49.73; H, 5.63; N, 26.05 IR(KBr) cm$^{-1}$: 3350, 1678, 1622, 1587 NMR(CDCl$_3$) δ (ppm): 4.92(2H, brs), 4.32(2H, t, J=7 Hz), 3.34(2H, t, J=7 Hz), 1.68(9H, s) MS(m/e): 265(M$^+$), 209

EXAMPLE 14

3-Amino-6,7-dihydro-2-(2,2,2-trifluoroethyl)pyrazolo[3,4-d]thiazolo[3,2-a]pyrimidin-4(2H)-one (Compound 18)

In 100 ml of propanol was dissolved 1.40 g (6.6 mmol) of the compound prepared in Reference Example 3, and 1.65 ml (13.1 mmol) of 2,2,2-trifluoroethylhydrazine (70% aqueous solution) was added to the solution, followed by heating under reflux for 3 hours. After evaporation of the solvent, the residue was subjected to partition between chloroform and water, and the chloroform layer was concentrated to dryness under reduced pressure. The residue was recrystallized from methanol to give 1.10 g (58%) of Compound 18 in pure form.

Melting Point: 285.2°–287.9° C. Elemental Analysis (%): $C_9H_8N_5OS$ Calcd.: C, 37.12; H, 2.77; N, 24.05 Found: C, 37.34; H, 2.61; N, 23.75 IR(KBr) cm$^{-1}$: 3390, 1658, 1261, 1155 NMR(DMSO-d$_6$) δ (ppm): 6.82(1H, brs), 4.90(2H, q, J=9 Hz), 4.23(2H, t, J=7 Hz), 3.45(2H, t, J=7 Hz) MS(m/e): 291(M$^+$), 249

EXAMPLE 15

3-Amino-6,7-dihydro-2-methoxycarbonylpyrazolo[3,4-d]thiazolo[3,2-a]pyrimidin-4(2H)-one (Compound 19)

In 110 ml of ethanol was dissolved 2.22 g (10.4 mmol) of the compound prepared in Reference Example 3, and 1.87 g (20.8 mmol) of methyl carbazate was added to the solution, followed by heating under reflux for 30 minutes. After evaporation of the solvent, the residue was subjected to partition between chloroform and water, and the chloroform layer was concentrated to dryness under reduced pressure. The residue was recrystallized from ethanol to give 2.2 g (79%) of Compound 19 in pure form.

Melting Point: 200.5°–202.6° C. Elemental Analysis (%): $C_9H_9N_5O_3S$ Calcd.: C, 40.45; H, 3.39; N, 26.20 Found: C, 40.51; H, 3.14; N, 26.25 IR(KBr) cm$^{-1}$: 3240, 1736, 1666, 1562 NMR(DMSO-d$_6$) δ (ppm): 9.77(2H, brs), 4.29(2H, t, J=8 Hz), 3.63(3H, s), 3.53(2H, t, J=8 Hz) MS(m/e): 267(M$^+$), 223

EXAMPLE 16

3-Acetylamino-6,7-dihydro-1-methylpyrazolo[3,4-d]thiazolo[3,2-a]pyrimidin-4(1H)-one (Compound 20)

In 20 ml of pyridine was dissolved 2.00 g (8.96 mmol) of Compound 13 prepared in Example 10, and 1.23 ml (13.0 mmol) of acetic anhydride was added to the solution, followed by stirring at 50° C. for 6 hours. After evaporation of the solvent, the residue was subjected to partition between chloroform and water. The chloroform layer was washed with a dilute aqueous solution of hydrochloric acid and water, and concentrated to dryness under reduced pressure. The residue was recrystallized from chloroform/ethanol to give 1.46 g (62%) of Compound 20 in pure form.

Melting Point: 249.8°–251.9° C. Elemental Analysis (%): $C_{10}H_{11}N_5O_2S \cdot 0.2H_2O$ Calcd.: C, 44.67; H, 4.27; N, 26.05 Found: C, 44.77; H, 3.98; N, 25.88 IR(KBr) cm$^{-1}$: 1663, 1558 NMR(CDCl$_3$) δ (ppm): 8.10(1H, brs), 4.46(2H, t, J=7 Hz), 3.85(3H, s), 3.52(2H, t, J=7 Hz), 2.28(3H, brs) MS(m/e): 265(M$^+$), 223

EXAMPLE 17

3-Benzoylamino-6,7-dihydro-1-methylpyrazolo[3,4-d]thiazolo[3,2-a]pyrimidin-4(1H)-one (Compound 21)

In 14 ml of pyridine was dissolved 1.40 g (6.27 mmol) of Compound 13 prepared in Example 10, and 0.80 ml (6.9 mmol) of benzoyl chloride was added to the solution, followed by stirring at 50° C. for 30 minutes. After evaporation of the solvent, the residue was subjected to partition between chloroform and water. The chloroform layer was washed with a dilute aqueous solution of hydrochloric acid and water, and concentrated to dryness under reduced pressure. The residue was recrystallized from chloroform/ethanol to give 1.81 g (80%) of Compound 21 in pure form.

Melting Point: 271.1°–271.7° C. Elemental Analysis (%): $C_{15}H_{13}N_5O_2S$ Calcd.: C, 55.03; H, 4.00; N, 21.40 Found: C, 54.95; H, 3.83; N, 21.08 IR(KBr) cm$^{-1}$: 1674, 1543, 1508 NMR(CDCl$_3$) δ (ppm): 8.99(1H, brs), 7.99–7.95(2H, m), 7.60–7.47(3H, m), 4.47(2H, t, J=7 Hz), 3.91(3H, s), 3.54(2H, t, J=7 Hz) MS(m/e): 327(M$^+$), 298

EXAMPLE 18

3-(N-Acetyl-N-methyl)amino-6,7-dihydro-1-methylpyrazolo[3,4-d]thiazolo[3,2-a]pyrimidin-4(1H)-one (Compound 22)

In 70 ml of dimethylformamide was dissolved 2.32 g (8.74 mmol) of Compound 20 prepared in Example 16, and 0.63 g (15.8 mmol) of sodium hydride (60%) and 1.23 ml (19.8 mmol) of methyl iodide were added to the solution, followed by stirring at room temperature for one hour. After addition of water and evaporation of the solvent, the residue was subjected to partition between chloroform and water. The chloroform layer was concentrated to dryness under reduced pressure to give 2.44 g (100%) of Compound 22. The compound was recrystallized from ethanol for purification.

Melting Point: 211.3°–212.6° C. Elemental Analysis (%): $C_{11}H_{13}N_5O_2S\cdot 0.1H_2O$ Calcd.: C, 47.00; H, 4.73; N, 24.91 Found: C, 47.13; H, 4.57; N, 24.57 IR(KBr) cm$^{-1}$: 1692, 1676, 1562, 1526, 1376 NMR(CDCl$_3$) δ (ppm): 4.49(2H, t, J=7 Hz), 3.88(3H, s), 3.54(2H, t, J=7 Hz), 3.33(3H, s), 2.04(3H, s) MS(m/e): 279(M$^+$), 237

EXAMPLE 19

6,7-Dihydro-1-methyl-3-methylaminopyrazolo[3,4-d]thiazolo[3,2-a]pyrimidin-4(1H)-one (Compound 23)

In a mixture of 300 ml of dioxane and 75 ml of 2N hydrochloric acid was dissolved 2.44 g (8.74 mmol) of Compound 22 prepared in Example 18, followed by heating under reflux for 2 hours. After evaporation of the solvent, the residue was subjected to partition between chloroform and water, and the chloroform layer was concentrated to dryness under reduced pressure. The residue was subjected to silica gel column chromatography and eluted with chloroform-methanol (50:1). The main fraction was recrystallized from chloroform/ethanol to give 1.11 g (54%) of Compound 23 in pure form.

Melting Point: 254.6°–255.5° C. Elemental Analysis (%): $C_9H_{11}N_5OS$ Calcd.: C, 45.55; H, 4.67; N, 29.52 Found: C, 45.86; H, 4.62; N, 29.14 IR(KBr) cm$^{-1}$: 1668, 1561, 1519 NMR(CDCl$_3$) δ (ppm): 4.42(2H, t, J=7 Hz), 3.72(3H, s), 3.48(2H, t, J=7 Hz), 2.98(3H, s) MS(m/e): 237(M$^+$), 209

EXAMPLE 20

3-Chloro-6,7-dihydro-1-methylpyrazolo[3,4-d]thiazolo[3,2-a]pyrimidin-4(1H)-one (Compound 24)

In a mixture of 45 ml of hydrochloric acid and 30 ml of water was dissolved 3.35 g (15.0 mmol) of Compound 13 prepared in Example 10, and 1.05 g (15.2 mmol) of sodium nitrite was added to the solution under ice-cooling, followed by stirring for 30 minutes. Then, a solution of 1.80 g (18.2 mmol) of cuprous chloride in 30 ml of hydrochloric acid was added thereto and the temperature of the mixture was raised slowly to room temperature, followed by stirring for one hour. The precipitated crystals were collected by filtration and then washed with water, followed by recrystallization from chloroform/ethanol to give 2.64 g (73%) of Compound 24.

Melting Point: 221.7°–222.4° C. Elemental Analysis (%): $C_8H_7ClN_4OS$ Calcd.: C, 39.59; H, 2.91; N, 23.09 Found: C, 39.67; H, 2.76; N, 23.22 IR(KBr) cm$^{-1}$: 1685, 1560, 1506 NMR(CDCl$_3$) δ (ppm): 4.49(2H, t, J=7 Hz), 3.85(3H, s), 3.52(2H, t, J=7 Hz) MS(m/e): 242(M$^+$), 183

EXAMPLE 21

3-Bromo-6,7-dihydro-1-methylpyrazolo[3,4-d]thiazolo[3,2-a]pyrimidin-4(1H)-one (Compound 25)

In a mixture of 52 ml of an aqueous solution of hydrogen bromide and 36 ml of water was dissolved 4.00 g (17.9 mmol) of Compound 13 prepared in Example 10, and 1.24 g (17.9 mmol) of sodium nitrite was added to the solution under ice-cooling, followed by stirring for 30 minutes. Then, a solution of 3.08 g (21.5 mmol) of cuprous bromide in 36 ml of an aqueous solution of hydrogen bromide was added thereto and the temperature of the mixture was raised slowly to room temperature, followed by stirring for one hour. The precipitated crystals were collected by filtration and washed with water. The crystals were then subjected to silica gel column chromatography and eluted with chloroform to give 3.51 g (68%) of Compound 25. The compound was recrystallized from chloroform/ethanol for purification.

Melting Point: 205.2°–205.6° C. Elemental Analysis (%): $C_8H_7BrN_4OS$ Calcd.: C, 33.46; H, 2.46; N, 19.52 Found: C, 33.78; H, 2.35; N, 19.44 IR(KBr) cm$^{-1}$: 1688, 1531, 1493 NMR(CDCl$_3$) δ (ppm): 4.49(2H, t, J=7 Hz), 3.87(3H, s), 3.52(2H, t, J=7 Hz) MS(m/e): 286(M$^+$), 107

EXAMPLE 22

6,7-Dihydro-1-ethylpyrazolo[3,4-d]thiazolo[3,2-a]pyrimidin-4(1H)-one (Compound 26)

6,7-Dihydro-2-ethylpyrazolo[3,4-d]thiazolo[3,2-a]pyrimidin-4(2H)-one (Compound 27)

In 40 ml of dimethylformamide was dissolved 2.07 g (10.7 mmol) of Compound 1 prepared in Example 1, and 0.77 g (19.3 mmol) of sodium hydride (60%) and 2.56 ml (32.0 mmol) of ethyl iodide were added to the solution, followed by stirring at room temperature for 6 hours. After addition of water and evaporation of the solvent, the residue was subjected to partition between chloroform and water, and the chloroform layer was concentrated to dryness under reduced pressure. The residue was subjected to silica gel column chromatography and eluted with chloroform-methanol (100:1). The first and second main fractions gave 1.24 g (53%) of Compound 26 and 0.51 g (22%) of Compound 27, respectively. Compound 26 and Compound 27 were recrystallized from dimethylformamide/water and ethanol, respectively, for purification.

Compound 26

Melting Point: 214.2°–214.9° C. Elemental Analysis (%): $C_9H_{10}N_4OS$ Calcd.: C, 48.64; H, 4.53; N, 25.21 Found: C, 48.88; H, 4.36; N, 25.17 IR(KBr) cm$^{-1}$: 1699, 1546, 1532 NMR(CDCl$_3$) δ (ppm): 7.98(1H, s), 4.50(2H, t, J=7 Hz), 4.30(2H, q, J=7 Hz), 3.52(2H, t, J=7 Hz), 1.46(3H, t, J=7 Hz) MS(m/e): 222(M$^+$), 207, 194

Compound 27

Melting Point: 207.8°–208.8° C. Elemental Analysis (%): $C_9H_{10}N_4OS$ Calcd.: C, 48.64; H, 4.53; N, 25.21 Found: C, 48.50; H, 4.20; N, 25.05 IR(KBr) cm$^{-1}$: 1680, 1580, 1479 NMR(CDCl$_3$) δ (ppm): 7.98(1H, s), 4.45(2H, t, J=7 Hz), 4.28(2H, q, J=7 Hz), 3.45(2H, t, J=7 Hz), 1.57(3H, t, J=7 Hz) MS(m/e): 222(M$^+$), 207, 194

EXAMPLE 23

6,7-Dihydro-1-n-propylpyrazolo[3,4-d]thiazolo[3,2-a]pyrimidin-4(1H)-one (Compound 28)

6,7-Dihydro-2-n-propylpyrazolo[3,4-d]thiazolo[3,2-a]pyrimidin-4(2H)-one (Compound 29)

In 50 ml of dimethylformamide was dissolved 2.50 g (12.9 mmol) of Compound 1 prepared in Example 1, and 0.93 g (23.3 mmol) of sodium hydride (60%) and 3.77 ml (38.6 mmol) of propyl iodide were added to the solution, followed by stirring at room temperature for one hour. After addition of water and evaporation of the solvent, the residue was subjected to partition between chloroform and water, and the chloroform layer was concentrated to dryness under reduced pressure. The residue was subjected to silica gel column chromatography and eluted with chloroform-methanol (100:1). The first and second main fractions gave 1.95 g (64%) of Compound 28 and 0.75 g (25%) of Compound 29, respectively. Each compound was recrystallized from ethanol for purification.

Compound 28

Melting Point: 176.2°–177.6° C. Elemental Analysis (%): $C_{10}H_{12}N_4OS$ Calcd.: C, 50.83; H, 5.12; N, 23.71 Found: C, 50.66; H, 5.03; N, 23.69 IR(KBr) cm$^{-1}$: 1703, 1550, 1505 NMR(CDCl$_3$) δ (ppm): 7.98(1H, s), 4.50(2H, t, J=7 Hz), 4.21(2H, t, J=7 Hz), 3.51(2H, t, J=7 Hz), 1.90(2H, q, J=7 Hz), 0.91(3H, t, J=7 Hz) MS(m/e): 236(M$^+$), 207, 194

Compound 29

Melting Point: 146.2°–147.6° C. Elemental Analysis (%): $C_{10}H_{12}N_4OS$ Calcd.: C, 50.83; H, 5.12; N, 23.71 Found: C, 50.84; H, 5.11; N, 23.80 IR(KBr) cm$^{-1}$: 1683, 1584, 1478 NMR(CDCl$_3$) δ (ppm): 7.96(1H, s), 4.45(2H, t, J=7 Hz), 4.18(2H, t, J=7 Hz), 3.44(2H, t, J=7 Hz), 1.97(2H, q J=7 Hz), 0.92(3H, t, J=7 Hz) MS(m/e): 236(M$^+$), 207, 194

EXAMPLE 24

6,7-Dihydro-1-isopropylpyrazolo[3,4-d]thiazolo[3,2-a]pyrimidin-4(1H)-one (Compound 30)

6,7-Dihydro-2-isopropylpyrazolo[3,4-d]thiazolo[3,2-a]pyrimidin-4(2H)-one (Compound 31)

In 50 ml of dimethylformamide was dissolved 2.50 g (12.9 mmol) of Compound 1 prepared in Example 1, and 0.77 g (19.3 mmol) of sodium hydride (60%) and 1.92 ml (19.3 mmol) of isopropyl iodide were added to the solution, followed by stirring at room temperature for 2 hours. After addition of water and evaporation of the solvent, the residue was subjected to partition between chloroform and water, and the chloroform layer was concentrated to dryness under reduced pressure. The residue was subjected to silica gel column chromatography and eluted with chloroform-methanol (100:1). The first and second main fractions gave 1.89 g (62%) of Compound 30 and 8.88 g (29%) of Compound 31, respectively. Each compound was recrystallized from ethanol for purification.

Compound 30

Melting Point: 177.2°–177.4° C. Elemental Analysis (%): $C_{10}H_{12}N_4OS$ Calcd.: C, 50.83; H, 5.12; N, 23.71 Found: C, 50.83; H, 4.91; N, 23.94 IR(KBr) cm$^{-1}$: 1700, 1553, 1526 NMR(CDCl$_3$) δ (ppm): 7.99(1H, s), 4.94(1H, m), 4.50(2H, t, J=7 Hz), 3.51(2H, t, J=7 Hz), 1.51(3H, d, J=7 Hz) MS(m/e): 236(M$^+$), 221, 194

Compound 31

Melting Point: 159.3°–159.9° C. Elemental Analysis (%): $C_{10}H_{12}N_4OS$ Calcd.: C, 50.83; H, 5.12; N, 23.71 Found: C, 50.78; H, 4.89; N, 24.00 IR(KBr) cm$^{-1}$: 1696, 1581, 1480 NMR(CDCl$_3$) δ (ppm): 8.01(1H, s), 4.58(1H, m), 4.45(2H, t, J=7 Hz), 3.44(2H, t, J=7 Hz), 1.57(3H, d, J=7 Hz) MS(m/e): 236(M$^+$), 221, 194

EXAMPLE 25

6,7-Dihydro-1-n-butylpyrazolo[3,4-d]thiazolo[3,2-a]pyrimidin-4(1H)-one (Compound 32)

6,7-Dihydro-2-n-butylpyrazolo[3,4-d]thiazolo[3,2-a]pyrimidin-4(2H)-one (Compound 33)

In 50 ml of dimethylformamide was dissolved 2.50 g (12.9 mmol) of Compound 1 prepared in Example 1, and 0.77 g (19.3 mmol) of sodium hydride (60%) and 2.20 ml (19.3 mmol) of butyl iodide were added to the solution, followed by stirring at room temperature for one hour. After addition of water and evaporation of the solvent, the residue was subjected to partition between chloroform and water, and the chloroform layer was concentrated to dryness under reduced pressure. The residue was subjected to silica gel column chromatography and eluted with chloroform-methanol (100:1). The first and second main fractions gave 2.30 g (71%) of Compound 32 and 0.84 g (26%) of Compound 33, respectively. Each compound was recrystallized from ethanol for purification.

Compound 32

Melting Point: 178.0°–178.5° C. Elemental Analysis (%): $C_{11}H_{14}N_4OS$ Calcd.: C, 52.78; H, 5.63; N, 22.38 Found: C, 52.69; H, 5.53; N, 22.42 IR(KBr) cm$^{-1}$: 1717, 1558, 1506 NMR(CDCl$_3$) δ (ppm): 7.97(1H, s), 4.50(2H, t, J=7 Hz), 4.24(2H, t, J=7 Hz), 3.51(2H, t, J=7 Hz), 1.91–1.80(2H, m), 1.39–1.25(2H, m), 0.94(3H, t, J=7 Hz) MS(m/e): 250(M$^+$), 207

Compound 33

Melting Point: 122.5°–122.9° C. Elemental Analysis (%): $C_{11}H_{14}N_4OS$ Calcd.: C, 52.78; H, 5.63; N, 22.38 Found: C, 52.61; H, 5.72; N, 22.48 IR(KBr) cm$^{-1}$: 1695, 1573, 1478 NMR(CDCl$_3$) δ (ppm): 7.95(1H, s), 4.45(2H, t, J=7 Hz), 4.21(2H, t, J=7 Hz), 3.44(2H, t, J=7 Hz), 1.98–1.87(2H, m), 1.39–1.25(2H, m), 0.94(3H, t, J=7 Hz) MS(m/e): 250(M$^+$), 207

EXAMPLE 26

6,7-Dihydro-1-tert-butoxycarbonylmethylpyrazolo[3,4-d]thiazolo[3,2-a]pyrimidin-4(1H)-one (Compound 34)

6,7-Dihydro-2-tert-butoxycarbonylmethylpyrazolo[3,4-d]thiazolo[3,2-a]pyrimidin-4(2H)-one (Compound 35)

In 120 ml of dimethylformamide was dissolved 3.00 g (15.4 mmol) of Compound 1 prepared in Example 1, and 1.86 g (46.3 mmol) of sodium hydride (60%) and 7.48 ml (46.3 mmol) of tert-butyl bromoacetate were added to the solution, followed by stirring at 50° C. for 12 hours. After addition of water and evaporation of the solvent, the residue was subjected to partition between chloroform and water, and the chloroform layer was concentrated to dryness under reduced pressure. The residue was subjected to silica gel column chromatography and eluted with chloroform-methanol (100:1). The first and second main fractions gave 1.59 g (33%) of Compound 34 and 0.97 g (20%) of Compound 35, respectively. Each compound was recrystallized from ethanol for purification.

Compound 34

Melting Point: 162.5°–163.1° C. Elemental Analysis (%): $C_{13}H_{16}N_4O_3S$ Calcd.: C, 50.64; H, 5.23; N, 18.17 Found: C, 50.40; H, 5.26; N, 18.10 IR(KBr) cm$^{-1}$: 1745, 1693, 1563, 1542 NMR(CDCl$_3$) δ (ppm): 8.03(1H, s), 4.93(2H, s), 4.50(2H, t, J=7 Hz), 3.51(2H, t, J=7 Hz), 1.47(9H, s) MS(m/e): 308(M$^+$), 207

Compound 35

Melting Point: 186.1°–186.4° C. Elemental Analysis (%): $C_{13}H_{16}N_4O_3S$ Calcd.: C, 50.64; H, 5.23; N, 18.17 Found: C, 50.45; H, 5.24; N, 18.22 IR(KBr) cm$^{-1}$: 1738, 1693, 1579 NMR(CDCl$_3$) δ (ppm): 8.06(1H, s), 4.90(2H, s), 4.45(2H, t, J=7 Hz), 3.44(2H, t, J=7 Hz), 1.47(9H, s) MS(m/e): 308(M$^+$), 207

EXAMPLE 27

1-Carboxymethyl-6,7-dihydropyrazolo[3,4-d]thiazolo[3,2-a]pyrimidin-4(1H)-one (Compound 36)

In 30 ml of trifluoroacetic acid was dissolved 1.18 g (3.83 mmol) of Compound 34 prepared in Example 26, followed by heating under reflux for one hour. After evaporation of the solvent, water was added to the residue. The precipitated crystals were collected by filtration, followed by washing with water to give 0.61 g (63%) of Compound 36. The compound was recrystallized from ethanol for purification.

Melting Point: 212.3°–214.2° C. Elemental Analysis (%): $C_9H_8N_4O_3S \cdot 0.5C_2H_5OH$ Calcd.: C, 43.63; H, 4.03; N, 20.35 Found: C, 43.44; H, 3.74; N, 20.26 IR(KBr) cm$^{-1}$: 3114, 1728, 1629, 1589 NMR(DMSO-d$_6$) δ (ppm): 13.21(1H, brs), 8.02(1H, s), 4.99(2H, s), 4.39(2H, t, J=7 Hz), 3.60(2H, t, J=7 Hz) MS(m/e): 252(M$^+$), 207

EXAMPLE 28

2-Carboxymethyl-6,7-dihydropyrazolo[3,4-d]thiazolo[3,2-a]pyrimidin-4(2H)-one (Compound 37)

In 30 ml of trifluoroacetic acid was dissolved 0.95 g (3.08 mmol) of Compound 35 prepared in Example 26, followed by heating under reflux for one hour. After evaporation of the solvent, water was added to the residue. The precipitated crystals were collected by filtration, followed by washing with water to give 0.54 g (70%) of Compound 37. The compound was recrystallized from dimethylformamide/water for purification.

Melting Point: 276.2°–276.4° C. Elemental Analysis (%): $C_9H_8N_4O_3S$ Calcd.: C, 42.85; H, 3.20; N, 22.21 Found: C, 42.91; H, 2.95; N, 21.95 IR(KBr) cm$^{-1}$: 3400, 1714, 1676, 1561 NMR(DMSO-d$_6$) δ (ppm): 13.29(1H, brs), 8.46(1H, s), 5.08(2H, s), 4.33(2H, t, J=7 Hz), 3.51(2H, t, J=7 Hz) MS(m/e): 252(M$^+$), 207

EXAMPLE 29

6,7-Dihydro-1-methylpyrrolo[2,3-d]thiazolo[3,2-a]pyrimidin-4(1H)-one (Compound 38)

In 34 ml of methanesulfonic acid was dissolved 3.39 g (12.5 mmol) of the compound prepared in Reference Example 8, followed by stirring at 120° C. for one hour. After cooling, the reaction solution was poured onto ice and neutralized with an aqueous solution of sodium hydroxide, followed by partition between chloroform and water. After the organic layer was concentrated to dryness under reduced pressure, the residue was subjected to silica gel column chromatography and eluted with chloroform-methanol (100:1) to give 1.55 g (60%) of Compound 38. The compound was recrystallized from ethanol for purification.

Melting Point: 176.3°–176.8° C. Elemental Analysis (%): $C_9H_9N_3O_3S$ Calcd.: C, 52.16; H, 4.38; N, 20.28 Found: C, 51.94; H, 4.28; N, 19.99 IR(KBr) cm$^{-1}$: 1625, 1544, 1500 NMR(CDCl$_3$) δ (ppm): 6.69(1H, d, J=3 Hz), 6.58(1H, d, J=3 Hz), 4.51(2H, t, J=7 Hz), 3.69(3H, s), 3.48(2H, t, J=7 Hz) MS(m/e): 207(M$^+$), 165

EXAMPLE 30

6,7-Dihydro-1-methylpyrazolo[3,4-d]thiazolo[3,2-a]pyrimidin-4(1H)-thione (Compound 39)

In 50 ml of toluene was dissolved 2.08 g (10.0 mmol) of Compound 2 prepared in Example 2, and 4.45 g (11.0 mmol) of Lawesson's reagent was added to the solution, followed by heating under reflux for 30 minutes. After cooling, the precipitated crystals were collected by filtration, and then washed with toluene. The crystals were subjected to silica gel column chromatography and eluted with chloroform to give 1.90 g (85%) of Compound 39. The compound was recrystallized from chloroform/ethanol for purification.

Melting Point: 199.3°–199.8° C. Elemental Analysis (%): $C_8H_8N_4S_2$ Calcd.: C, 42.84; H, 3.59; N, 24.98 Found: C, 42.81; H, 3.26; N, 24.61 IR(KBr) cm$^{-1}$: 1568, 1503, 1443, 1412 NMR(CDCl$_3$) δ (ppm): 8.09(1H, s), 4.88(2H, t, J=7 Hz), 3.90(3H, s), 3.56(2H, t, J=7 Hz) MS(m/e): 224(M$^+$), 191

EXAMPLE 31

6,7-Dihydro-1,6-dimethylpyrazolo[3,4-d]thiazolo[3,2-a]pyrimidin-4(1H)-one (Compound 40)

In 100 ml of dimethylformamide was dissolved 5.0 g (27.4 mmol) of 4,5-dihydro-6-mercapto-1-methylpyrazolo[3,4-d]pyrimidin-4(1H)-one [Helv. Chim. Acta, 42, 349 (1959)], and 15.1 g (109 mmol) of potassium carbonate and 5.7 ml (54.5 mmol) of 1,2-dibromopropane were added to the solution, followed by stirring at 80° C. for 12 hours. After evaporation of the solvent, the residue was subjected to partition between chloroform and water, and the chloroform layer was concentrated to dryness under reduced pressure. The residue was subjected to silica gel column chromatography and eluted with chloroform-methanol (100:1) to give 1.56 g (26%) of Compound 40. The compound was recrystallized from ethanol for purification.

Melting Point: 194.8°–195.7° C. Elemental Analysis (%): $C_9H_{10}N_4OS$ Calcd.: C, 48.64; H, 4.53; N, 25.21 Found: C, 48.71; H, 4.27; N, 25.05 IR(KBr) cm$^{-1}$: 1691, 1560, 1509 NMR(CDCl$_3$) δ (ppm): 7.96(1H, s), 5.30–5.20(1H, m), 3.91(3H, s), 3.82(1H, dd, J=8 Hz, 11 Hz), 3.03(1H, d, J=11 Hz), 1.55(3H, d, J=7 Hz) MS(m/e): 222(M$^+$), 207

EXAMPLE 32

6,7-Dihydro-1,6,7-trimethylpyrazolo[3,4-d]thiazolo[3,2-a]pyrimidin-4(1H)-one (Compound 41)

In 200 ml of dimethylformamide was dissolved 10.0 g (54.9 mmol) of 4,5-dihydro-6-mercapto-1-methylpyrazolo[3,4-d]pyrimidin-4(1H)-one [Helv. Chim. Acta, 42, 349 (1959)], and 15.2 g (110 mmol) of potassium carbonate and 10.1 ml (82.3 mmol) of 2,3-dibromobutane were added to the solution, followed by stirring at 80° C. for 3 hours. After evaporation of the solvent, the residue was subjected to partition between chloroform and water, and the chloroform layer was concentrated to dryness under reduced pressure. The residue was subjected to silica gel column chromatography and eluted with chloroform to give 1.57 g (12%) of Compound 41. The compound was recrystallized from ethyl acetate/hexane for purification.

Melting Point: 168.2°–169.8° C. Elemental Analysis (%): $C_{10}H_{12}N_4OS$ Calcd.: C, 50.83; H, 5.12; N, 23.71 Found: C, 50.74; H, 4.90; N, 23.85 IR(KBr) $cm^{-1}$: 1690, 1550, 1498 NMR(CDCl$_3$) δ (ppm): 7.96(1H, s), 5.12–5.02(1H, m), 4.40(1H, m), 3.91(3H, s), 1.48(3H, d, J=7 Hz), 1.40(3H, d, J=7 Hz) MS(m/e): 236($M^+$), 221

EXAMPLE 33

6,7-Dihydro-7-ethoxycarbonyl-1-methylpyrazolo[3,4-d]thiazolo[3,2-a]pyrimidin-4(1H)-one (Compound 42)

In 150 ml of dimethylformamide was dissolved 8.42 g (46.2 mmol) of 4,5-dihydro-6-mercapto-1-methylpyrazolo[3,4-d]pyrimidin-4(1H)-one [Helv. Chim. Acta, 42, 349 (1959)], and 12.8 g (92.4 mmol) of potassium carbonate and 18.0 ml (69.3 mmol) of ethyl 2,3-dibromopropionate were added to the solution, followed by stirring at 80° C. for 6 hours. After evaporation of the solvent, the residue was subjected to partition between chloroform and water, and the chloroform layer was concentrated to dryness under reduced pressure. The residue was subjected to silica gel column chromatography and eluted with chloroform to give 3.16 g (24%) of Compound 42. The compound was recrystallized from ethanol for purification.

Melting Point: 159.3°–159.5° C. Elemental Analysis (%): $C_{11}H_{12}N_4O_3S$ Calcd.: C, 47.14; H, 4.31; N, 19.99 Found: C, 47.26; H, 4.20; N, 20.10 IR(KBr) $cm^{-1}$: 173 8, 1694, 1562, 1516 NMR(CDCl$_3$) δ (ppm): 7.98(1H, s), 4.90(1H, dd, J=8 Hz, 15 Hz), 4.54–4.45(2H, m), 4.28(2H, q, J=7 Hz), 3.91(3H, s), 1.32(3H, t, J=7 Hz) MS(m/e): 280($M^+$), 207

EXAMPLE 34

7-Carboxy-6,7-dihydro-1-methylpyrazolo[3,4-d]thiazolo[3,2-a]pyrimidin-4(1H)-one (Compound 43)

In a mixture of 50 ml of dioxane and 14 ml of water was dissolved 1.30 g (6.24 mmol) of Compound 42 prepared in Example 33, and 0.52 g (12.5 mmol) of lithium hydroxide was added to the solution, followed by stirring at room temperature for 30 minutes. After evaporation of the solvent, the residue was dissolved in water, and then hydrochloric acid was added. The precipitated crystals were collected by filtration, and washed with water, followed by recrystallization from dimethylformamide/water to give 1.09 g (69%) of Compound 43.

Melting Point: 274.4°–276.4° C. Elemental Analysis (%): $C_9H_8N_4O_3S$•$0.2H_2O$ Calcd.: C, 42.25; H, 3.31; N, 21.90 Found: C, 42.36; H, 3.09; N, 21.55 IR(KBr) $cm^{-1}$: 3098, 1696, 1566, 1516 NMR(DMSO-d$_6$) δ (ppm): 7.99(1H, s), 4.76(1H, dd, J=5 Hz, 8 Hz), 4.62(1H, dd, J=5 Hz, 12 Hz), 4.38(1H, dd, J=8 Hz, 12 Hz), 3.82(3H, s) MS(m/e): 252($M^+$), 207

EXAMPLE 35

7,8-Dihydro-1-methyl-6H-pyrazolo[3',4':4,5]pyrimido[2,1-b]-[1,3]thiazin-4(1H)-one (Compound 44)

In 80 ml of dimethylformamide was dissolved 4.0 g (22.0 mmol) of 4,5-dihydro-6-mercapto-1-methylpyrazolo[3,4-d]pyrimidin-4(1H)-one [Helv. Chim. Acta, 42, 349 (1959)], and 9.1 g (66 mmol) of potassium carbonate and 3.34 ml (32.9 mmol) of 1,3-dibromopropane were added to the solution, followed by stirring at 80° C. for 8 hours. After evaporation of the solvent, the residue was subjected to partition between chloroform and water, and the chloroform layer was concentrated to dryness under reduced pressure. The residue was subjected to silica gel column chromatography and eluted with chloroform-methanol (100:1) to give 1.87 g (38%) of Compound 44. The compound was recrystallized from ethanol for purification.

Melting Point: 179.2°–179.9° C. Elemental Analysis (%): $C_9H_{10}N_4OS$ Calcd.: C, 48.64; H, 4.53; N, 25.21 Found: C, 48.79; H, 4.33; N, 25.12 IR(KBr) $cm^{-1}$: 1686, 1556, 1151, 770 NMR(CDCl$_3$) δ (ppm): 7.97(1H, s), 4.20–4.10(2H, m), 3.91(3H, s), 3.26(2H, t, J=6 Hz), 2.33–2.24(2H, m) MS(m/e): 222($M^+$), 207

EXAMPLE 36

1-Methyl-6,7,8,9-tetrahydropyrazolo[3',4':4,5]pyrimido[2,1-b]-[1,3]thiazepin-4(1H)-one (Compound 45)

In 120 ml of dimethylformamide was dissolved 6.0 g (32.9 mmol) of 4,5-dihydro-6-mercapto-1-methylpyrazolo[3,4-d]pyrimidin-4(1H)-one [Helv. Chim. Acta, 42, 349 (1959)], and 13.7 g (98.8 mmol) of potassium carbonate and 5.90 ml (49.4 mmol) of 1,4-dibromobutane were added to the solution, followed by stirring at 80° C. for 6 hours. After evaporation of the solvent, the residue was subjected to partition between chloroform and water, and the chloroform layer was concentrated to dryness under reduced pressure. The residue was subjected to silica gel column chromatography and eluted with chloroform to give 1.71 g (22%) of Compound 45. The compound was recrystallized from ethanol for purification.

Melting Point: 157.2°–157.4° C. Elemental Analysis (%): $C_{10}H_{12}N_4OS$ Calcd.: C, 50.83; H, 5.12; N, 23.71 Found: C, 50.86; H, 4.95; N, 23.93 IR(KBr) $cm^{-1}$: 1684, 1548, 1499 NMR(CDCl$_3$) δ (ppm):8.02(1H, s), 4.58–4.55(2H, m), 3.98(3H, s), 3.12–3.08(2H, m), 2.14–1.93(4H, m) MS(m/e): 236($M^+$), 207

EXAMPLE 37

6,7-Dihydro-1,7-dimethylpyrazolo[3,4-d]thiazolo[3,2-a]pyrimidin-4(1H)-one (Compound 46)

In 40 ml of acetic acid saturated with hydrogen chloride was dissolved 2.47 g (11.1 mmol) of the compound prepared in Reference Example 10, followed by heating under reflux for 6 hours. The reaction solution was subjected to partition between chloroform and water, and the chloroform layer was concentrated to dryness under reduced pressure. The residue was subjected to silica gel column chromatography and eluted with chloroform-methanol (100:1) to give 1.48 g (60%) of Compound 46. The compound was recrystallized from ethanol for purification.

Melting Point: 178.1°–179.0° C. Elemental Analysis (%): $C_9H_{10}N_4OS$ Calcd.: C, 48.64; H, 4.53; N, 25.21 Found: C, 48.56; H, 4.36; N, 24.91 IR(KBr) $cm^{-1}$: 1686, 1559, 1511 NMR(CDCl$_3$) δ (ppm): 7.96(1H, s), 4.58–4.51(1H, m), 4.18–4.03(2H, m), 3.91(3H, s), 1.59(3H, d, J=6 Hz) MS(m/e): 222($M^+$), 207

EXAMPLE 38

6,7-Dihydro-1,7,7-trimethylpyrazolo[3,4-d]thiazolo[3,2-a]pyrimidin-4(1H)-one (Compound 47)

In 80 ml of acetic acid saturated with hydrogen chloride was dissolved 3.23 g (13.7 mmol) of the compound prepared in Reference Example 11, followed by heating under reflux for 6 hours. The reaction solution was subjected to partition between chloroform and water, and the chloroform layer was concentrated to dryness under reduced pressure. The residue was recrystallized from ethanol to give 2.45 g (76%) of Compound 47 in pure form.

Melting Point: 187.5°–188.1° C. Elemental Analysis (%): $C_{10}H_{12}N_4OS$ Calcd.: C, 50.83; H, 5.12; N, 23.71 Found: C, 50.91; H, 5.16; N, 23.49 IR(KBr) $cm^{-1}$: 1686, 1558, 1510 NMR(CDCl$_3$) δ (ppm): 7.97(1H, s), 4.24(2H, s), 3.92(3H, s), 1.68(6H, s) MS(m/e): 236($M^+$), 221, 203

EXAMPLE 39

6,7-Dihydro-1,6,6-trimethylpyrazolo[3,4-d]thiazolo[3,2-a]pyrimidin-4(1H)-one (Compound 48)

In 40 ml of methylene chloride was dissolved 4.0 g (18.9 mmol) of the compound prepared in Reference Example 9, and 2.17 ml (22.7 mmol) of 2-amino-2-methyl-1-propanol was added to the solution, followed by stirring at room temperature for 30 minutes. After evaporation of the solvent, a 2N aqueous solution of sodium hydroxide was added to the residue, followed by washing with ethyl acetate. The aqueous layer was neutralized by addition of hydrochloric acid and then concentrated. The precipitated crystals were collected by filtration, and dissolved in 100 ml of methanesulfonic acid. After stirring at 120° C. for one hour, the reaction solution was poured onto ice, and then neutralized with an aqueous solution of sodium hydroxide, followed by extraction with chloroform. The organic layer was concentrated to dryness under reduced pressure, and the residue was subjected to silica gel column chromatography and eluted with chloroform-methanol (100:1). Recrystallization from ethanol gave 0.92 g (20%) of Compound 48.

Melting Point: 187.5°–188.1° C. Elemental Analysis (%): $C_{10}H_{12}N_4OS$ Calcd.: C, 50.83; H, 5.12; N, 23.71 Found: C, 50.97; H, 5.15; N, 23.60 IR(KBr) $cm^{-1}$: 1691, 1562, 1509 NMR(CDCl$_3$) δ (ppm): 7.93(1H, s), 3.90(3H, s), 3.28(2H, s), 1.83(6H, s) MS(m/e): 236($M^+$), 221, 203

EXAMPLE 40

6,7-Dihydro-6,7-diphenyl-1-methylpyrazolo[3,4-d]thiazolo[3,2-a]pyrimidin-4(1H)-one (Compound 49)

In 20 ml of methylene chloride was dissolved 2.0 g (9.5 mmol) of the compound prepared in Reference Example 9, and 2.0 g (9.5 mmol) of 2-amino-1,2-diphenylethanol was added to the solution, followed by stirring at room temperature for 30 minutes. After evaporation of the solvent, a 2N aqueous solution of sodium hydroxide was added to the residue, followed by washing with ethyl acetate. The aqueous layer was neutralized by addition of hydrochloric acid and then concentrated. The precipitated crystals were collected by filtration, and dissolved in 100 ml of methanesulfonic acid. After stirring at 120° C. for one hour, the reaction solution was poured onto ice, and then neutralized with an aqueous solution of sodium hydroxide, followed by extraction with chloroform. The organic layer was concentrated to dryness under reduced pressure, and the residue was subjected to silica gel column chromatography and eluted with chloroform. Recrystallization from ethyl acetate/hexane gave 2.18 g (64%) of Compound 49.

Melting Point: 158.9°–159.4° C. Elemental Analysis (%): $C_{20}H_{16}N_4OS$ Calcd.: C, 66.64; H, 4.47; N, 15.55 Found: C, 66.60; H, 4.37; N, 15.29 IR(KBr) $cm^{-1}$: 1695, 1556, 1509 NMR(CDCl$_3$) δ (ppm): 7.96(1H, s), 7.46–7.28(10H, m), 6.09(1H, d, J=1 Hz), 4.71(1H, f, J=1 Hz), 4.00(3H, s) MS(m/e): 360($M^+$), 236

EXAMPLE 41

6,7-Dihydro-1-methyl-7-phenylpyrazolo[3,4-d]thiazolo[3,2-a]pyrimidin-4(1H)-one (Compound 50)

In 20 ml of methylene chloride was dissolved 2.0 g (9.5 mmol) of the compound prepared in Reference Example 9, and 2.0 g (10.4 mmol) of 2-chloro-2-phenylethylamine hydrochloride and 2.6 ml (19 mmol) of triethylamine were added to the solution, followed by stirring at room temperature for one hour. To the reaction solution was added a 2N aqueous solution of sodium hydroxide, followed by extraction of the organic layer. After the organic layer was concentrated to dryness under reduced pressure, the residue was subjected to silica gel column chromatography and eluted with chloroform. Recrystallization from ethanol gave 1.64 g (61%) of Compound 50.

Melting Point: 190.8°–191.0° C. Elemental Analysis (%): $C_{14}H_{12}N_4OS$ Calcd.: C, 59.14; H, 4.25; N, 19.70 Found: C, 59.18; H, 4.10; N, 19.57 IR(KBr) $cm^{-1}$: 1686, 1563, 1557, 1513 NMR(CDCl$_3$) δ (ppm): 7.99(1H, s), 7.47–7.36(5H, m), 5.16(1H, dd, J=8 Hz, 8 Hz), 4.85(1H, dd, J=8 Hz, 13 Hz), 4.47(1H, dd, J=8 Hz, 13 Hz), 3.94(3H, s) MS(m/e): 284($M^+$), 251

EXAMPLE 42

1-Methylpyrazolo[3,4-d]thiazolo[3,2-a]pyrimidin-4(1H)-one (Compound 51)

In 8 ml of phosphorus oxychloride was dissolved 2.00 g (11.9 mmol) of 5-oxo-5H-thiazolo[3,2-a]pyrimidine [Zh. Org. Khim., 11, 2200 (1975)], and 1.13 ml of dimethylformamide was added dropwise to the solution with stirring under ice-cooling. Then, the reaction mixture was heated under reflux for 30 minutes. After concentration of the reaction mixture to dryness under reduced pressure, the oily residue was dissolved in 60 ml of ethanol under ice-cooling. To the solution were added 10 ml of triethylamine and 2.52 ml (47.6 mmol) of methylhydrazine, followed by heating under reflux for 3 hours. After evaporation of the solvent, the residue was subjected to partition between chloroform and water, and the chloroform layer was concentrated to dryness under reduced pressure. The residue was subjected to silica gel column chromatography and eluted with chloroform to give 1.74 g (71%) of Compound 51. The compound was recrystallized from dimethylformamide/water for purification.

Melting Point: 220.3°–221.2° C. IR(KBr) cm$^{-1}$: 1730, 1559, 1505 NMR(CDCl$_3$) δ (ppm): 8.141(1H, s), 7.96(1H, d, J=5 Hz), 6.82(1H, d, J=5 Hz), 3.99(3H, s) MS(m/e): 206(M$^+$), 151

Reference Example 1

7-Chloro-2,3-dihydro-5-oxo-5H-thiazolo[3,2-a]pyrimidine-6-carbaldehyde

In 40 ml of phosphorus oxychloride was dissolved 10.0 g (58.8 mmol) of 2,3-dihydro-7-hydroxy-5-oxo-5H-thiazolo [3,2 -a]pyrimidine [J. Am. Chem. Soc., 64, 2709 (1942)], and 6.0 ml of dimethylformamide was added dropwise to the solution with stirring under ice-cooling. Then, the reaction mixture was heated under reflux for 30 minutes. After concentration of the reaction mixture to dryness under reduced pressure, the oily residue was poured by portions into ice water. The precipitated crystals were collected by filtration, and recrystallized from chloroform to give 8.8 g (69%) of the desired compound as pale yellow crystals.

Melting Point: 152.0°–154.5° C. Elemental Analysis (%): C$_7$H$_5$ClN$_2$O$_2$S Calcd.: C, 38.81; H, 2.33; N, 12.93 Found: C, 38.77; H, 2.19; N, 12.63 IR(KBr) cm$^{-1}$: 1720, 1671, 1471 NMR(CDCl$_3$) δ (ppm): 10.25(1H, s), 4.58(2H, t, J=8 Hz), 3.60(2H, t, J=8 Hz) MS(m/e): 216(M$^+$), 188

Reference Example 2

7-Chloro-2,3-dihydro-5-oxo-5H-thiazolo[3,2-a]pyrimidine-6-carbaldehyde oxime

In 100 ml of ethanol was dissolved 3.7 g (1.7 mmol) of the compound prepared in Reference Example 1, and 1.65 g (2.4 mmol) of hydroxylamine hydrochloride was added to the solution, followed by stirring at room temperature for one hour. After the reaction was completed, the precipitated crystals were collected by filtration to give 2.0 g (51%) of the desired compound.

Melting Point: 148.5°–150.0° C. Elemental Analysis (%): C$_7$H$_6$ClN$_3$O$_2$S Calcd.: C, 36.29; H, 2.61; N, 18.14 Found: C, 3 6.22; H, 2.28; N, 17.91 IR(KBr) cm$^{-1}$: 3240, 1663, 1501 NMR(DMSO-d$_6$) δ (ppm): 11.4(1H, brs), 7.95(1H, s), 4.37(2H, t, J=8 Hz), 3.58(2H, t, J=8 Hz) MS(m/e): 231(M$^+$), 213, 195

Reference Example 3

7-Chloro-2,3-dihydro-5-oxo-5H-thiazolo[3,2-a]pyrimidine-6-carbonitrile

In 370 ml of tetrahydrofuran was dissolved 18.4 g (79.4 mmol) of the compound prepared in Reference Example 2, and ml of phosphorus oxychloride was added dropwise to the solution with stirring under ice-cooling. Then, the reaction mixture was stirred at room temperature for one hour. After evaporation of the solvent, diisopropyl ether was added to the residue and the precipitated crystals were collected by filtration. The crystals were subjected to silica gel column chromatography and eluted with chloroform-methanol (50:1) to give 18.5 g (86%) of the desired compound.

Melting point: 148.0°–149.5° C. Elemental Analysis (%): C$_7$H$_4$ClN$_3$OS Calcd.: C, 39.35; H, 1.89; N, 19.67 Found: C, 39.45; H, 1.56; N, 19.57 IR(KBr) cm$^{-1}$: 2226, 1680, 1494 NMR(DMSO-d$_6$) δ (ppm): 4.41(2H, t, J=8 Hz), 3.65(2H, t, J=8 Hz) MS(m/e): 213(M$^+$)

Reference Example 4

7-Chloro-2,3-dihydro-6-(1-hydroxyethyl)-5-oxo-5H-thiazolo[3,2-a]pyrimidine

In 200 ml of tetrahydrofuran was dissolved 6.24 g (28.8 mmol) of the compound prepared in Reference Example 1, and 11.5 ml (34.6 mmol) of methylmagnesium bromide (3M ether solution) was added to the solution under ice-cooling. The mixture was stirred at room temperature for 5 hours, followed by addition of an aqueous solution of ammonium chloride and chloroform. After concentration of the organic layer to dryness under reduced pressure, the residue was subjected to silica gel column chromatography and eluted with chloroform to give 4.56 g (68%) of the desired compound.

Melting Point: 170.9°–171.5 ° C. Elemental Analysis (%): C$_8$H$_9$ClN$_2$O$_2$S Calcd.: C, 41.30; H, 3.90; N, 12.04 Found: C, 41.29; H, 3.80; N, 11.94 IR(KBr) cm$^{-1}$: 3388, 1652, 1561, 1518 NMR(CDCl$_3$) δ (ppm): 5.00–4.80(1H, m), 4.44(2H, t, J=7 Hz), 3.48(2H, t, J=7 Hz), 1.42(3H, d, J=7 Hz) MS(m/e): 232(M$^+$), 217

Reference Example 5

6-Acetyl-7-chloro-2,3-dihydro-5-oxo-5H-thiazolo[3,2-a]pyrimidine

In 20 ml of acetone was dissolved 2.00 g (8.6 mmol) of the compound prepared in Reference Example 4, and a solution in which 1.72 g (17.2 mmol) of chromium oxide was dissolved in a mixture of 1.9 ml of sulfuric acid and 8.6 ml of water was added under ice-cooling until no starting material remained. After the reaction was completed, the temperature of the mixture was raised to room temperature. The mixture was concentrated to reduce the amount of acetone to half under reduced pressure, followed by partition between chloroform and water. After concentration of the chloroform layer to dryness under reduced pressure, the residue was subjected to silica gel column chromatography and eluted with chloroform to give 1.20 g (61%) of the desired compound.

Melting Point: 134.6°–136.1° C. Elemental Analysis (%): C$_8$H$_7$ClN$_2$O$_2$S Calcd.: C, 41.66; H, 3.06; N, 12.14 Found: C, 41.85; H, 2.84; N, 11.88 IR(KBr) cm$^{-1}$: 1687, 1647, 1542, 1497 NMR(CDCl$_3$) δ (ppm): 4.50(2H, t, J=8 Hz), 3.55(2H, t, J=8 Hz), 2.52(3H, s) MS(m/e): 230(M$^+$), 215

Reference Example 6

7-Chloro-6-{1-(4-chlorophenyl)-1-hydroxymethyl}-2,3-dihydro-5-oxo-5H-thiazolo[3,2-a]pyrimidine In 200 ml of tetrahydrofuran was dissolved 4.33 g (20.0 mmol) of the compound prepared in Reference Example 1, and 25.0 ml (25.0 mmol) of 4-chlorophenylmagnesium bromide (1M ether solution) was added to the solution under ice-cooling. The mixture was stirred at room temperature for 6 hours, followed by addition of an aqueous solution of ammonium chloride and chloroform. After concentration of the organic layer to dryness under reduced pressure, the residue was subjected to silica gel column chromatography and eluted with chloroform to give 3.44 g (52%) of the desired compound.

Melting Point: 174.8°–176.8° C. Elemental Analysis (%): C$_{13}$H$_{10}$C$_{12}$N$_2$O$_2$S Calcd.: C, 47.43; H, 3.06; N, 8.51 Found: C, 47.51; H, 3.03; N, 8.37 IR(KBr) cm$^{-1}$: 3325, 1672, 1562, 1521 NMR(CDCl$_3$) δ (ppm): 7.43–7.26(4H, m), 5.92(1H, d, J=12 Hz), 5.04(1H, d, J=12 Hz), 4.44(2H, t, J=7 Hz), 3.51(2H, t, J=7 Hz) MS(m/e): 328(M$^+$), 310

Reference Example 7

7-Chloro-6-(4-chlorobenzoyl)-2,3-dihydro-5-oxo-5H-thiazolo[3,2-a]pyrimidine

In 20 ml of acetone was dissolved 1.65 g (5.0 mmol) of the compound prepared in Reference Example 6, and a solution in which 0.91 g (9.2 mmol) of chromium oxide was dissolved in a mixture of 1.0 ml of sulfuric acid and 4.5 ml of water was added under ice-cooling until no starting material remained. After the reaction was completed, the temperature of the mixture was raised to room temperature. The mixture was concentrated to reduce the amount of acetone to half under reduced pressure, followed by partition between chloroform and water. The chloroform layer was concentrated to dryness under reduced pressure to give 1.61 g (98%) of the desired compound.

Melting Point: 174.2°–174.5° C. Elemental Analysis (%): $C_{13}H_8C_{12}N_2O_2S$ Calcd.: C, 47.72; H, 2.46; N, 8.56 Found: C, 47.95; H, 2.24; N, 8.17 IR(KBr) cm$^{-1}$: 1651, 1588, 1561, 1510 NMR(CDCl$_3$) δ (ppm): 7.87–7.82(2H, m), 7.47–7.42(2H, m), 4.48(2H, t, J=7 Hz), 3.55(2H, t, J=7 Hz) MS(m/e): 326(M$^+$), 291, 215

Reference Example 8

2,3-Dihydro-7-[N-(2,2-dimethoxyethyl)-N-methyl]amino-5-oxo-5H-thiazolo[3,2-a]pyrimidine In 6 ml of phosphorus oxychloride was dissolved 2.50 g (14.7 mmol) of 2,3-dihydro-7-hydroxy-5-oxo-5H-thiazolo[3,2-a]pyrimidine [J. Am. Chem. Soc., 64, 2709 (1942)], followed by heating under relfux for 30 minutes. After the reaction solution was concentrated to dryness under reduced pressure, the oily residue was poured by portions into ice water. The precipitated crystals were collected by filtration, and dissolved in 50 ml of ethanol. To the solution was added 3.76 ml (29.4 mmol) of methylaminoacetaldehyde dimethylacetal, followed by heating under reflux for 6 hours. After evaporation of the solvent, the residue was subjected to partition between chloroform and water, and then the chloroform layer was concentrated to dryness under reduced pressure. The residue was subjected to silica gel column chromatography and eluted with chloroform to give 3.394 g (85%) of the desired compound. The compound was recrystallized from ethyl acetate/hexane for purification.

Melting Point: 75.0°–78.3° C. Elemental Analysis (%): $C_{11}H_{17}N_3O_3S \cdot 0.9H_2O$ Calcd.: C, 45.95; H, 6.57; N, 14.61 Found: C, 46.11; H, 6.59; N, 14.61 IR(KBr) cm$^{-1}$: 1636, 1573, 1534, 1419 NMR(CDCl$_3$) δ (ppm): 5.09(1H, s), 4.47–4.40(3H, m), 3.58(2H, d, J=5 Hz), 3.43–3.36(8H, m), 2.99(3H, s) MS(m/e): 271(M$^+$), 256

Reference Example 9

Ethyl 5-isothiocyanate-1-methylpyrazole-4-carboxylate

In 600 ml of chloroform was dissolved 63.4 g (375 mmol) of ethyl 5-amino-1-methylpyrazole-4-carboxylate [Helv. Chim. Acta., 42, 349 (1959)], and 28.5 ml (374 mmol) of thiophosgene was added to the solution, followed by heating under reflux for 6 hours. After cooling, the precipitated crystals were filtered and washed with chloroform. After concentration of the combined washings and filtrate to dryness under reduced pressure, the residue was subjected to silica gel column chromatography and eluted with chloroform to give 23.6 g (30%) of the desired compound. The compound was recrystallized from hexane for purification.

Melting Point: 55.7°–56.0° C. Elemental Analysis (%): $C_8H_9N_3O_2S$ Calcd.: C, 45.49; H, 4.29; N, 19.89 Found: C, 45.64; H, 4.15; N, 19.96 IR(KBr) cm$^{-1}$: 2086, 1704, 1386, 1208 NMR(CDCl$_3$) δ (ppm): 7.80(1H, s), 4.33(2H, q, J=7 Hz), 3.81(3H, s), 1.38(3H, t, J=7 Hz) MS(m/e): 211(M$^+$), 166

Reference Example 10

5-Allyl-6-mercapto-1-methylpyrazolo[3,4-d]pyrimidin-4(1H)-one

In 40 ml of methylene chloride was dissolved 4.0 g (18.9 mmol) of the compound prepared in Reference Example 9, and 1.70 ml (22.7 mmol) of allylamine was added to the solution, followed by stirring at room temperature for 30 minutes. After evaporation of the solvent, a 2N aqueous solution of sodium hydroxide was added, followed by washing with ethyl acetate. After addition of hydrochloric acid to the aqueous layer, the precipitated crystals were collected by filtration, and then washed with water to give 2.56 g (61%) of the desired compound.

Melting Point: 171.4°–173.8° C. Elemental Analysis (%): $C_9H_{10}N_4OS$ Calcd.: C, 48.64; H, 4.53; N, 25.21 Found: C, 48.53; H, 4.44; N, 25.08 IR(KBr) cm$^{-1}$: 3112, 1687, 1608, 1194 NMR(DMSO-d$_6$) δ (ppm): 13.7(1H, brs), 7.94(1H, s), 5.93–5.81(1H, m), 5.14–4.99(2H, m), 3.88(3H, s) MS(m/e): 222(M$^+$), 207

Reference Example 11

5-(2-Methyl-2-propenyl)-6-mercapto-1-methylpyrazolo[3,4-d]pyrimidin-4(1H)-one

In 40 ml of methylene chloride was dissolved 4.0 g (18.9 mmol) of the compound prepared in Reference Example 9, and 2.24 g (20.8 mmol) of 2-methylallylamine hydrochloride and 5.3 ml (38 mmol) of triethylamine were added to the solution, followed by stirring at room temperature for 30 minutes. After evaporation of the solvent, a 2N aqueous solution of sodium hydroxide was added, followed by washing with ethyl acetate. After addition of hydrochloric acid to the aqueous layer, the precipitated crystals were collected by filtration, and then washed with water to give 3.20 g (72%) of the desired compound.

Melting Point: 157.6°–159.8° C. Elemental Analysis (%): $C_9H_{10}N_4OS$ Calcd.: C, 48.64; H, 4.53; N, 25.21 Found: C, 48.53; H, 4.44; N, 25.08 IR(KBr) cm$^{-1}$: 3025, 1675, 1610, 1177 NMR(DMSO-d$_6$) δ (ppm): 13.7(1H, brs), 7.96(1H, s), 4.87(2H, s), 4.78(1H, s), 4.41(1H, s), 3.90(3H, s), 1.73(3H, s) MS(m/e): 236(M$^+$), 221

Preparation Example 1

Tablets

Tablets each having the following composition are prepared in a conventional manner.

| | |
|---|---|
| Compound 1 | 50 mg |
| Lactose | 113 mg |
| Potato Starch | 30 mg |
| Hydroxypropylcellulose | 6 mg |
| Magnesium Stearate | 0.6 mg |

Preparation Example 2

Capsules

Capsules each having the following composition are prepared in a conventional manner.

| | |
|---|---|
| Compound 2 | 50 mg |
| Avicel | 69.5 mg |
| Magnesium Stearate | 0.5 mg |

A mixture of the above ingredients is loaded into gelatin capsules.

Industrial Applicability

According to the present invention, there can be provided pyrazolothiazolopyrimidine derivatives which are useful as anti-inflammatory, immunomodulatory and anti-ulcer agents.

We claim:

1. A pyrazolothiazolopyrimidine derivative represented by the following Formula (I):

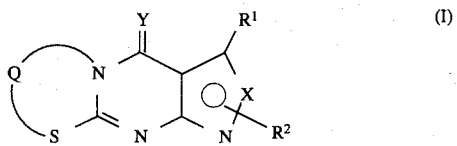

in which $R^1$ represents hydrogen, substituted or unsubstituted lower alkyl, substituted or unsubstituted aryl, substituted or unsubstituted aralkyl, halogen or $-NR^3R^4$ (in which $R^3$ and $R^4$ represent independently hydrogen, lower alkyl, lower alkanoyl or aroyl); when $R^2$ is a substituent on the 1-position, X represents N or CH, and $R^2$ represents hydrogen, substituted or unsubstituted lower alkyl, substituted or unsubstituted aryl, substituted or unsubstituted aralkyl or lower alkoxycarbonyl; when $R^2$ is a substituent on the 2-position, X represents N, and $R^2$ represents $-CR^5R^6R^7$ (in which $R^5$ represents substituted or unsubstituted lower alkyl; and $R^6$ and $R^7$ represent independently hydrogen or lower alkyl), substituted or unsubstituted aryl, substituted or unsubstituted aralkyl or lower alkoxycarbonyl; Y represents O or S; Q represents $-C^8R^9CR^{10}R^{11}-(CH_2)_n-$ or $-CR^8=CR^9-(CH_2)_n-$ (in which $R^8$, $R^9$, $R^{10}$ and $R^{11}$ represent independently hydrogen, substituted or unsubstituted lower alkyl, substituted or unsubstituted aryl, substituted or unsubstituted aralkyl or lower alkoxycarbonyl; and n is an integer of 0 to 2) or a pharmaceutically acceptable salt thereof.

* * * * *

UNITED STATES PATENT AND TRADEMARK OFFICE
CERTIFICATE OF CORRECTION

PATENT NO. : 5,527,908

DATED : June 18, 1996

INVENTOR(S) : FUMIO SUZUKI ET AL.

Page 1 of 2

It is certified that error appears in the above-identified patent and that said Letters Patent is hereby corrected as shown below:

COLUMN 2

Line 6, "fluorin," should read --fluorine,--.

COLUMN 6

Lne 11, "(i)" should read --(I)--.

COLUMN 9

Line 53, "(i)" should read --(I)--.

COLUMN 33

Line 54, "ml" should read --26 ml--.

UNITED STATES PATENT AND TRADEMARK OFFICE
CERTIFICATE OF CORRECTION

PATENT NO. : 5,527,908
DATED : June 18, 1996
INVENTOR(S) : FUMIO SUZUKI ET AL.

It is certified that error appears in the above-identified patent and that said Letters Patent is hereby corrected as shown below:

COLUMN 38

Lines 18-19, "$-C^8R^9CR^{10}R^{11}-(CH_2)_n-or-CR^8=CR^9-(CH_2)_n-(in$" should read
-- $-CR^8R^9CR^{10}R^{11}-(CH_2)_n-$ or $-CR^8=CR^9-(CH_2)_n-$ (in--.

Signed and Sealed this

Fourth Day of March, 1997

Attest:

BRUCE LEHMAN

Attesting Officer

Commissioner of Patents and Trademarks